US011266295B2

(12) United States Patent
Ueda et al.

(10) Patent No.: US 11,266,295 B2
(45) Date of Patent: Mar. 8, 2022

(54) ENDOSCOPE APPARATUS AND CONTROL METHOD OF ENDOSCOPE APPARATUS

(71) Applicant: SONY CORPORATION, Tokyo (JP)

(72) Inventors: Mitsunori Ueda, Tokyo (JP); Tomoyuki Oki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 426 days.

(21) Appl. No.: 16/311,076

(22) PCT Filed: Jun. 6, 2017

(86) PCT No.: PCT/JP2017/020998
§ 371 (c)(1),
(2) Date: Dec. 18, 2018

(87) PCT Pub. No.: WO2018/029962
PCT Pub. Date: Feb. 15, 2018

(65) Prior Publication Data
US 2019/0328207 A1 Oct. 31, 2019

(30) Foreign Application Priority Data

Aug. 8, 2016 (JP) .............................. JP2016-155896

(51) Int. Cl.
*A61B 1/00* (2006.01)
*A61B 1/045* (2006.01)
*A61B 1/06* (2006.01)

(52) U.S. Cl.
CPC ...... *A61B 1/00006* (2013.01); *A61B 1/00009* (2013.01); *A61B 1/00117* (2013.01);
(Continued)

(58) Field of Classification Search
CPC ............ A61B 1/00006; A61B 1/00096; A61B 1/00117; A61B 1/045; A61B 1/0623;
(Continued)

(56) References Cited

U.S. PATENT DOCUMENTS

| | | | |
|---|---|---|---|
| 4,953,937 A | 9/1990 | Kikuchi | |
| 2002/0128538 A1* | 9/2002 | Thompson | A61B 1/00039 600/121 |

(Continued)

FOREIGN PATENT DOCUMENTS

| | | |
|---|---|---|
| CN | 1242082 A | 1/2000 |
| CN | 101050844 A | 10/2007 |

(Continued)

OTHER PUBLICATIONS

Extended European Search Report dated Jul. 17, 2019 in corresponding European Application No. 17839037.3.

(Continued)

*Primary Examiner* — Aaron B Fairchild
(74) *Attorney, Agent, or Firm* — Xsensus LLP

(57) ABSTRACT

An endoscope apparatus includes: an endoscope at least a part of which is inserted into an observation object and that propagates an image of an inside of the observation object irradiated with illumination light; a light source that emits the illumination light illuminating the inside of the observation object to the endoscope; an imager that captures an image of the inside of the observation object having been propagated from the endoscope and generates a captured image of the inside of the observation object; and control circuitry that performs driving control for the endoscope, the light source, and the imager. The control circuitry is configured to change the radiation angle of the illumination light in accordance with whether an insertion portion being a part of the endoscope is moving in the inside of the observation object or as stopped.

16 Claims, 25 Drawing Sheets

(52) U.S. Cl.
CPC ............ *A61B 1/045* (2013.01); *A61B 1/0669* (2013.01); *A61B 1/00096* (2013.01); *A61B 1/0623* (2013.01)

(58) Field of Classification Search
CPC ........... A61B 1/07; A61B 1/0009; A61B 1/06; A61B 1/0661; A61B 1/0669; G02B 23/26
See application file for complete search history.

(56) References Cited

U.S. PATENT DOCUMENTS

| | | | |
|---|---|---|---|
| 2008/0161647 | A1 | 7/2008 | Pascal |
| 2008/0287742 | A1 | 11/2008 | St. George et al. |
| 2011/0273549 | A1* | 11/2011 | Kase ................. A61B 1/00177 348/68 |
| 2014/0012078 | A1 | 1/2014 | Coussa |

FOREIGN PATENT DOCUMENTS

| | | |
|---|---|---|
| CN | 101251709 A | 8/2008 |
| CN | 101636695 B | 6/2012 |
| CN | 202583663 U | 12/2012 |
| CN | 103519772 A | 1/2014 |
| CN | 103907042 A | 7/2014 |
| CN | 103988114 A | 8/2014 |
| CN | 204044437 U | 12/2014 |
| DE | 3623114 A1 | 1/1987 |
| EP | 2187259 A1 | 5/2010 |
| JP | H02148013 A | 6/1990 |
| JP | H10-239740 A | 9/1998 |
| JP | 2011147595 A * | 8/2011 |
| JP | 2015-136468 A | 7/2015 |
| JP | 5750422 B2 | 7/2015 |
| JP | 2016-505279 A | 2/2016 |
| JP | 2016-123825 A | 7/2016 |
| WO | 00/57770 A2 | 10/2000 |
| WO | WO-2010045406 A2 | 4/2010 |
| WO | WO 2011/055613 A1 | 5/2011 |

OTHER PUBLICATIONS

International Search Report dated Aug. 1, 2017 in PCT/JP2017/020998, 1 page.

Office Action dated Nov. 4, 2020 in Japanese Patent Application No. 2018-533439, 3 pages.

Etsuko Kobayashi, et al, A wide-angle view endoscope system using wedge prisms; Web of science, TS=(endoscope AND radiation angle) and TS=(mov* or locomot*).

"Journal of Yishui Medical College", No. 1 19820402 LU Donghaa (non official translation: Optical Fiber Light Guiding Principle and Medical Fiber Endoscope) 131-133.

* cited by examiner

FIG. 12
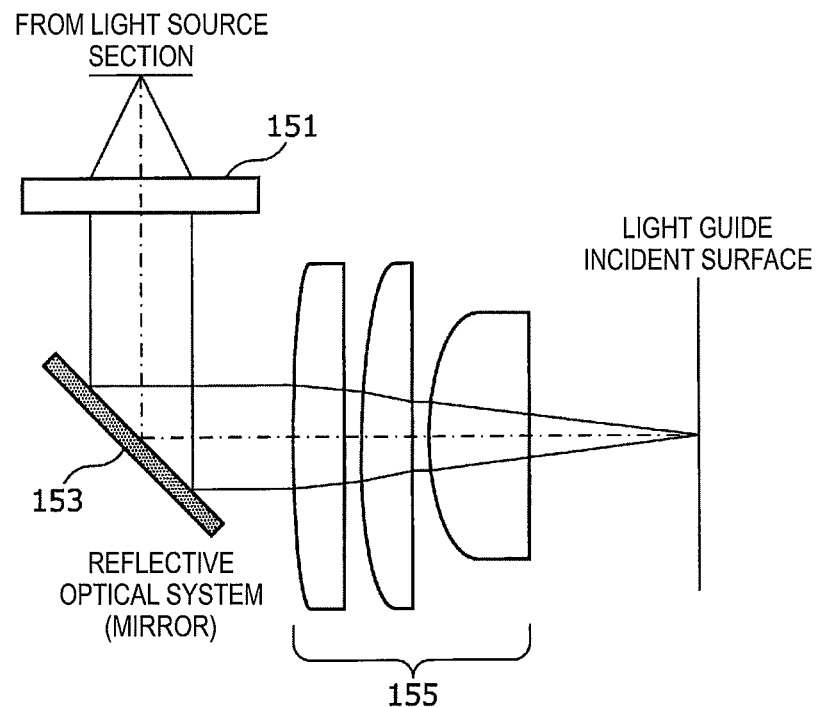
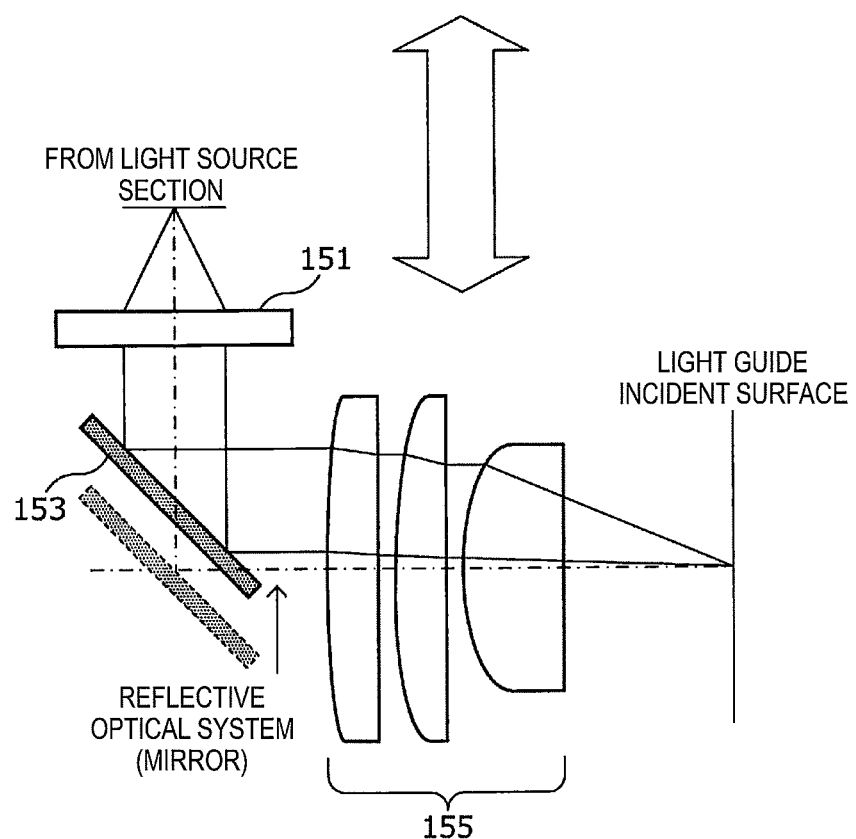

ENDOSCOPE APPARATUS AND CONTROL METHOD OF ENDOSCOPE APPARATUS

TECHNICAL FIELD

The present disclosure relates to an endoscope apparatus and a control method of an endoscope apparatus.

BACKGROUND ART

In recent years, various medical actions have been being performed using an endoscope apparatus disclosed in, for example, Patent Literature 1 shown below.

One of such the medical actions includes laparoscopic surgery and thoracoscopic surgery using rigid endoscopes in place of laparotomy and open chest surgery. Although these surgeries using rigid endoscopes are said to be less invasive for patients, for doctors being surgeons, there are many difficulties, such as strangulation of a visual field, lack of a stereoscopic effect, interference between other surgical instruments and camera due to working in narrow space, and interference with illumination. However, in recent years, along with the miniaturization, high definition of imaging elements, and making an imaging area to a wider angle, it becomes possible to increase a distance to an imaging object while keeping resolution constant. With this, while looking the picture in the same resolution as that in the past, it has become possible to execute working in a space much wider than that in the past.

Moreover, as one of other medical actions using endoscope apparatuses, there is observation of luminal organs by using flexible endoscopes. In the case where an image acquired by a flexible endoscope with regard to luminal organs is displayed on a display screen, the organs located at the back side are displayed on the center portion of the screen, and the organs located at the front side with a close distance from the flexible endoscope are displayed on a peripheral portion of the screen.

CITATION LIST

Patent Literature

Patent Literature 1: JP 5750422B

DISCLOSURE OF INVENTION

Technical Problem

Here, in the case of inserting the endoscope as described in the above into the inside of a body (i.e., a lumen, a body cavity, a body lumen, etc.) for the purpose of observation, diagnosis, imaging, or treatment, in order to reduce the pain or burden of a patient, it is important to cause a tip portion of the endoscope to be moved promptly to a target part.

However, in the case of inserting the tip portion of the endoscope while observing with using usual endoscope illumination, especially, in the case of inserting into a luminal organ, since a target part exists on the forward side of a lumen, it is difficult for illumination light to reach the target part. Accordingly, an image of a part to be inserted will become dark relatively. On the other hand, at the time of inserting the endoscope, with regard to an internal organ located on the way to a target part, since a distance from the tip portion of the endoscope is short, an amount of light of arriving illumination light becomes large, and an image becomes bright.

In a general endoscope apparatus, when a captured image is generated, control is performed such that a gain of an imaging signal changes with an average value or the maximum value of luminance within an imaging area as a reference (Auto Gain Control: AGC). Therefore, at the time of imaging, in the case where a bright region exists within an imaging region, in order to prevent the luminance of such a bright region from being saturated, an imaging control will be performed so as to lower the luminance of the whole image. As a result of the fact that such an AGC function functions, a captured image of an inner part of a lumen being an insertion target part is provided for an operator of an endoscope in a state of having become further darker.

With this, it becomes more difficult for the operator of the endoscope to observe the insertion target part of the endoscope, which may cause a possibility of damaging an inside of a body cavity. In order to reduce such a possibility and to avoid occurrence of bleeding, piercing, or the like, the insertion speed of the endoscope becomes further slow. Accordingly, since time required for inspection etc. is prolonged, there is a possibility that the mental burden and physical burden of a patient will increase.

Then, in the present disclosure, in view of the above-described situations, proposed are an endoscope apparatus and a control method of an endoscope apparatus in which it is possible to execute the insertion of an endoscope into an inside of an observation object more promptly, and it is possible to reduce the burden of an endoscope operator more.

Solution to Problem

According to the present disclosure, there is provided an endoscope apparatus, including: an endoscope unit at least a part of which is inserted into an inside of an observation object and that propagates an image of the inside of the observation object irradiated with illumination light; a light source unit that emits the illumination light illuminating the inside of the observation object to the endoscope unit; an imaging unit that captures an image of the inside of the observation object having been propagated from the endoscope unit and generates a captured image of the inside of the observation object; and a control section that performs driving control for the endoscope unit, the light source unit, and the imaging unit. A radiation angle of the illumination light is changeable, and the control section changes the radiation angle of the illumination light in accordance with whether an insertion portion being a part of the endoscope unit having been inserted into the inside of the observation object is moving in the inside of the observation object or has stopped.

In addition, according to the present disclosure, there is provided a control method of an endoscope apparatus that includes an endoscope unit at least a part of which is inserted into an inside of an observation object and that propagates an image of the inside of the observation object irradiated with illumination light, a light source unit that emits the illumination light illuminating the inside of the observation object to the endoscope unit, and an imaging unit that captures an image of the inside of the observation object having been propagated from the endoscope unit and generates a captured image of the inside of the observation object, in which a radiation angle of the illumination light is changeable, the control method including: by a control section that performs driving control for the endoscope unit, the light source unit, and the imaging unit, determining whether an insertion portion being a part of the endoscope unit having been inserted into the inside of the observation object is moving in the inside of the observation object or has stopped; and changing the radiation angle of the illumination light in accordance with a state of the insertion portion.

According to the present disclosure, a control section of an endoscope apparatus determines whether an insertion portion being a part of an endoscope unit inserted into an inside of an observation object is moving in the inside of the observation object or has stopped, and the radiation angle of illumination light is changed in accordance with a state of the insertion portion.

Advantageous Effects of Invention

As described in the above, according to the present disclosure, it is possible to execute the insertion of an endoscope into an inside of an observation object more promptly, and it is possible to reduce the burden of an endoscope operator more.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 12 is an explanatory illustration showing schematically the fourth concrete example of the coupling section according to the embodiment.

MODE(S) FOR CARRYING OUT THE INVENTION

Figure 1:
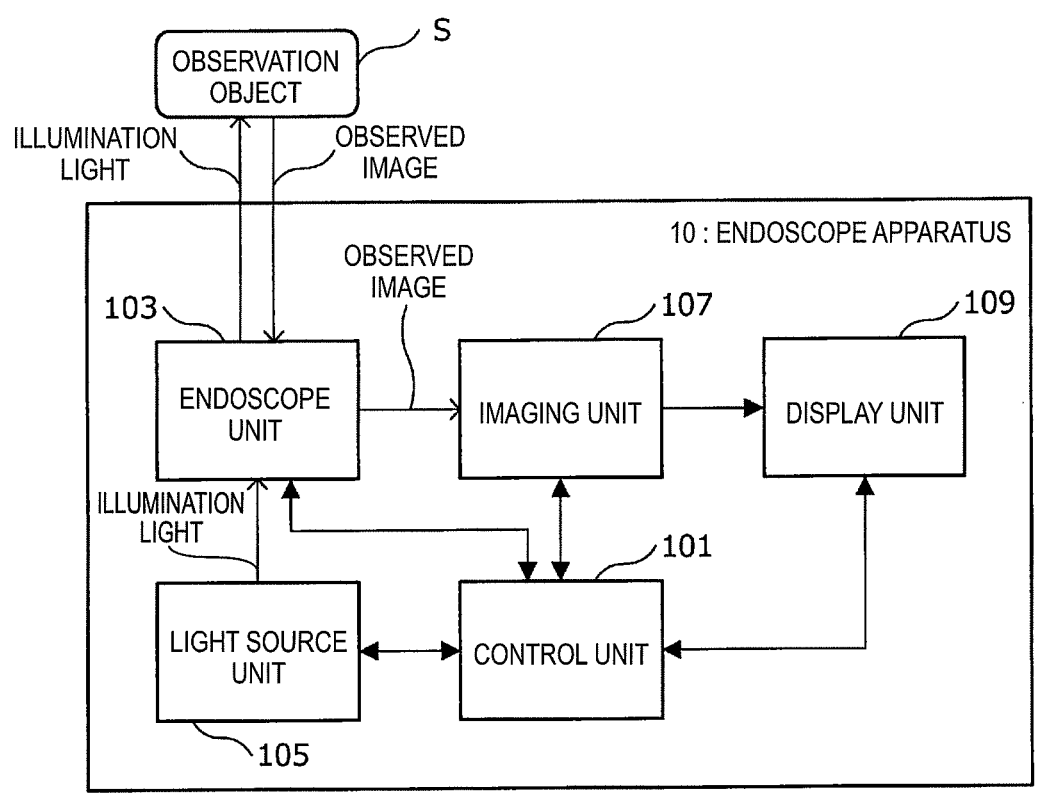
FIG. 1 is an explanatory diagram showing schematically an entire constitution of an endoscope apparatus according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

It should be noted that description is given in the following order.

1. Embodiment
   1.1. With regard to entire constitution of endoscope apparatus
   1.2. With regard to constitution of endoscope unit
   1.3. With regard to constitution of light source unit
   1.4. With regard to constitution of control unit
   1.5. With regard to hardware configuration of control unit Embodiment <With Regard to Entire Constitution of Endoscope Apparatus>

First, while referring to FIG. 1, an entire constitution of an endoscope apparatus according to an embodiment of the present disclosure is described briefly. FIG. 1 is an explanatory diagram showing schematically the entire constitution of the endoscope apparatus according to the present embodiment.

An endoscope apparatus 10 according to the present embodiment is an apparatus that can observe an inside of an observation object S through a part of it being inserted into the inside of the observation object S. As such an endoscope apparatus 10, for example, there are various kinds of medical endoscope apparatuses, such as a rigid endoscope, a flexible endoscope, and an arthroscope, various kinds of industrial endoscope apparatus, and so on.

In the below, it is assumed that description is given in detail by citing a case where the endoscope apparatus 10 is a medical endoscope apparatus and the observation object S is an inside (for example, a lumen, a body cavity, a body lumen, etc.) of a living body.

The endoscope apparatus 10 according to the present embodiment is an apparatus that generates a captured image of a living body S in a predetermined wavelength band by irradiating predetermined illumination light to a part of the living body S made an observing object and by imaging the part of the living body S irradiated with the observation light. Here, although the wavelength band of the illumination light is not limited specifically, generally, it is a visible light band (band corresponding to a range of a wavelength of about 380 nm to a wavelength of about 780 nm). Moreover, by changing the wavelength band of the illumination light, for example, it is also possible to generate a captured images in various kinds of wavelength bands, such as a captured image in a near-infrared band (band corresponding to a range of a wavelength of about 780 nm to a wavelength of about 2.5 μm) and a captured image in an ultraviolet ray band.

A captured image generated by the endoscope apparatus 10 with regard to the observation object is displayed at any time on a display unit, such as a display connected to the endoscope apparatus 10 through wires or wirelessly.

The endoscope apparatus 10 having such a function includes mainly, as shown schematically in FIG. 1, a control unit 101, an endoscope unit 103, a light source unit 105, an imaging unit 107, and a display unit 109.

The control unit 101 is realized by, for example, a CPU (Central Processing Unit), a ROM (Read Only Memory), a RAM (Random Access Memory), and the like. The control unit 101 is a unit which presides over and controls the overall function of the endoscope apparatus 10, and controls collectively the working states of the endoscope unit 103, the light source unit 105, the imaging unit 107, and the display unit 109, which constitute the endoscope apparatus 10. Such a control unit 101 is, for example, a unit corresponding to a camera control unit (CCU) of an endoscope apparatus.

The endoscope unit 103 is a unit a part of which is to be inserted into an inside of a living body under the control by the control unit 101. Such an endoscope unit 103 causes an image (observed image) obtained by observing an inside of the living body S by using the illumination light emitted from the light source unit 105 to be formed onto the imaging unit 107 at the latter stage.

The light source unit 105 is a unit that emits illumination light for observing an inside of a living body under the control by the control unit 101, and is optically connected to the endoscope unit 103. Such a light source unit 105 includes at least an illumination light source (for example, white light source etc.) for obtaining a captured image of a living body by using imaging elements. Moreover, in addition to such a light source, such a light source unit 105 may include various publicly-known light sources, such as a near-infrared light source for obtaining a captured image of a living body of a near-infrared band, an ultraviolet light source, and various kinds of laser light sources for emitting light of a specific wavelength. It is possible for the light source unit 105 to switch the kind of illumination light emitted from these various light sources at an arbitrary timing under the control of the control unit 101. Moreover, in addition to the light sources as described in the above, the light source unit 105 may further include, for example, a light source for realizing specific functions, such as a light source for OCT, a light source for distance measurement, and PDT (Photodynamic Therapy, photodynamic therapy).

The imaging unit 107 is a unit that generates image data of a captured image by capturing an observed image in an inside of a living body with illumination light from the light source unit 105 under the control by the control unit 101. Such an imaging unit 107 is optically connected to the endoscope unit 103.

In the endoscope apparatus 10, by using imaging elements that has sensitivity for wavelengths of a visible light band, an image close to a situation of being directly observed with human eyes is captured, and after such an image is appropriately developed, the observation result is displayed as a normal observed image on the display unit 109. Moreover, in a general endoscope apparatus capable of performing observation with special light, in addition to a normal observation mode that displays a captured image of a visible light band, realized are various kinds of functions, such as a fluorescence observation mode that observes fluorescence caused within a living body by using imaging elements having sensitivity also for wavelengths in a near-infrared band and a narrow-wavelength image (Narrow Band Imaging: NBI) observation mode that makes it easy to discriminate blood vessels different in depth from a skin surface by combining a plurality of specific narrow wavelengths.

The imaging unit 107 outputs the image data of a captured image generated as described in the above to the display unit 109 at the latter stage at any time under the control of the control unit 101.

The display unit 109 is a unit that displays a captured image generated by the imaging unit 107 for an operator of the endoscope apparatus 10 under the control by the control unit 101. The number of display screens disposed in such a display unit 109 is not limited specifically, and the display unit 109 may include only one display screen, and may include a plurality of display screens. Such a display unit 109 is not limited specifically, and it is possible to use a publicly-known display device.

In the above, while referring to FIG. 1, the entire constitution of the endoscope apparatus 10 according to the present embodiment has been described in detail. In this connection, since the endoscope apparatus 10 according to the present embodiment includes at least any of the endoscope unit 103 or the light source unit 105 as described in the below in detail, the radiation angle of illumination light becomes changeable.

<With Regard to Constitution of Endoscope Unit>

Figure 2A:
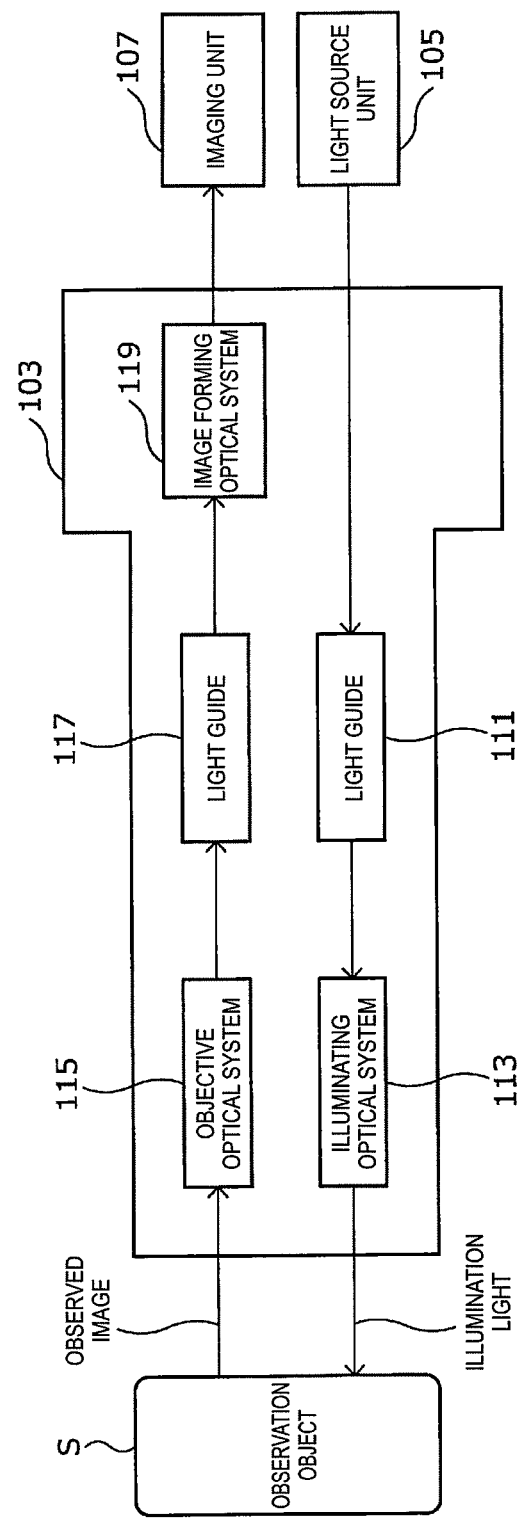
FIG. 2A is an explanatory diagram showing schematically one example of a constitution of an endoscope unit included by an endoscope apparatus according to the embodiment.
Figure 2B:
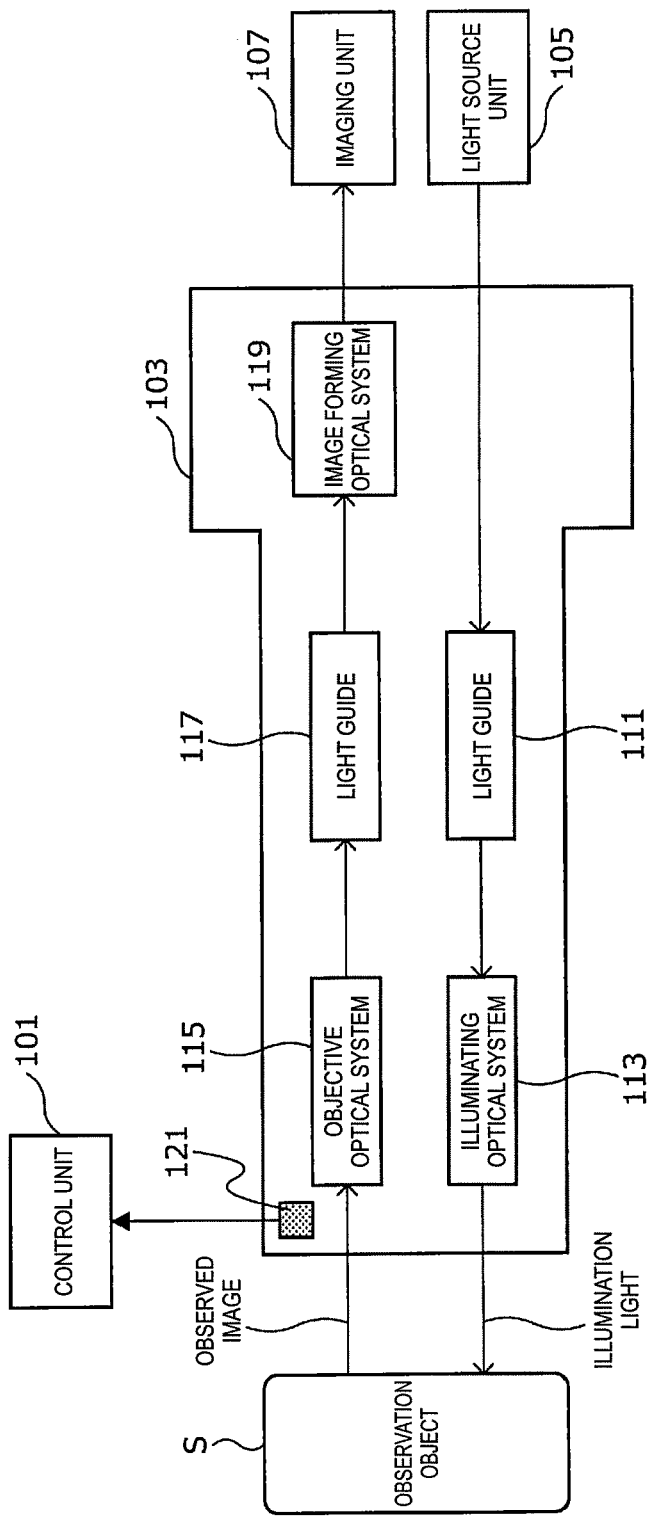
FIG. 2B is an explanatory diagram showing schematically one example of a constitution of an endoscope unit included by an endoscope apparatus according to the embodiment.
Figure 3:
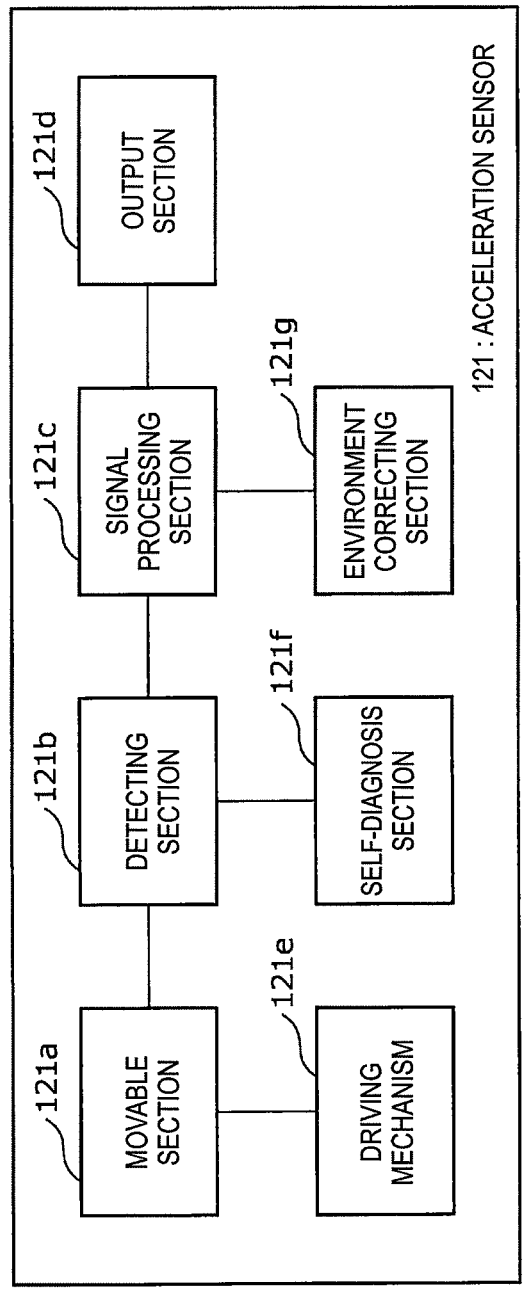
FIG. 3 is a block diagram showing schematically one example of the entire constitution of an acceleration sensor.

Next, while referring to FIG. 2A through FIG. 3, a constitution of the endoscope unit 103 included by the endoscope apparatus 10 according to the present embodiment, is described in detail. FIG. 2A and FIG. 2B each is an explanatory diagram showing schematically one example of a constitution of an endoscope unit included by the endoscope apparatus according to the present embodiment. FIG. 3 is a block diagram showing schematically one example of the entire constitution of an acceleration sensor.

The endoscope unit 103 according to the present embodiment is a unit at least a part of which is inserted into an inside of an observation object S and that propagates an image in the inside of the observation object S irradiated with illumination light to the imaging unit 107.

As schematically shown in FIG. 2A, such an endoscope unit 103 mainly includes relay optical systems 111 and 117, an illuminating optical system 113, an objective optical system 115, and an image forming optical system 119. As the relay optical system 117, in the case where the endoscope unit is a flexible endoscope, a light guide is used. However, in the case where the endoscope unit is a rigid endoscope, an optical system using a lens easy to maintain image quality is used. As the relay optical system 111 of an illuminating optical system, a light guide is usually used.

The light guide 111 as a relay optical system for illumination is one in which, usually, a plurality of index guide type multi-mode optical fibers with a core diameter of about 10 μm to 80 μm are bundled (bundled). The light guide 111 is connected to the light source unit 105, and guides illumination light (for example, illumination light in a visible light band) with predetermined wavelengths emitted from the light source unit 105 to a tip portion of the endoscope unit 103. Such a light guide 111 is not limited specifically, and, it is possible to use publicly-known various light guides.

The illuminating optical system 113 is an optical system that adjusts an image formation state of illumination light propagated by the light guide 111 onto an observation object S. Such an illuminating optical system 113 is not limited specifically, and it is possible to use publicly-known various illuminating optical systems.

Moreover, as having mentioned previously, the endoscope apparatus 10 according to the present embodiment is constituted such that the radiation angle of illumination light becomes changeable. In order to make the radiation angle of illumination light changeable, it is preferable that such an illuminating optical system 113 includes a mechanism for making the radiation angle of illumination light changeable, as disclosed in, for example, JP H1-185510A or JP H6-58458B. By moving at least some of optical elements (for example, various kinds of lenses etc.) of such an illuminating optical system 113 along the optical axis direction of the endoscope unit 103, it is possible to cause the radiation angle of illumination light to be changed.

In this connection, even in the case where the illuminating optical system 113 according to the present embodiment does not include the above-described mechanism for making the radiation angle of illumination lights changeable, it is sufficient that the light source unit 105 includes a mechanism for making the radiation angle of illumination light changeable as described in detail in the below.

The objective optical system 115 is an optical system for obtaining an observed image of a part that is located in the inside of the observation object S and is being irradiated with illumination light. Such an objective optical system 115 is not limited specifically, and, it is possible to use publicly-known various optical systems. The observed image propagated by the objective optical system 115 is further guided by the light guide 117 functioning as a relay optical system to the image forming optical system 119.

The image forming optical system 119 is an optical system for causing an observed image of an observation object S guided by the light guide 117 to be formed onto the imaging unit 107, and is optically connected with the imaging unit 107 at the latter stage. Such an image forming optical system 119 is not limited specifically, and, it is possible to use publicly-known various image forming optical systems.

In this connection, in the endoscope apparatus 10 according to the present embodiment, as mentioned in detail in the below, it is determined at any time whether an insertion portion being a part of an endoscope unit having been inserted in an inside of an observation object S is moving in the inside of the observation object S, or has stopped. In order for the control unit 101 of the endoscope apparatus 10 to execute such determination, as shown in FIG. 2B, in addition to the constitution shown in FIG. 2A, various kinds of acceleration sensors 121 may be disposed in the endoscope unit 103 according to the present embodiment.

Since such an acceleration sensor 121 is disposed in the endoscope unit 103, it is preferable that it is a MEMS (Micro Electro Mechanical Systems) type acceleration sensor that makes it possible to attain miniaturization. Moreover, the acceleration detection system of such an acceleration sensor is not limited specifically, and it is possible to use acceleration sensors conforming to various kinds of publicly-known principles, such as a capacitance detection system, a piezo-resistance system, and a heat detection system.

General acceleration sensors 121, including the MEMS type acceleration sensors, as schematically shown in FIG. 3, includes, in many cases, constitutions of a movable section 121a, a detecting section 121b, a signal processing section 121c, an output section 121d, a driving mechanism 121e, a self-diagnosis section 121f, and an environment correcting section 121g.

Upon receipt of an inertia force, a weight (weight, mass) included in the acceleration sensor is displaced by balance with the reaction force of an elastic body, such as a spring, supporting the weight (movable section 121a) The displacement of the movable section 121a is detected by a displacement detecting section attached to the weight, or a strain detecting section that detects the strain of the elastic body, such as a spring (detecting section 121b). An amount of displacement or an amount of strain detected by the detecting section 121b is converted into an electric signal by the signal processing section 121c. Such a signal processing section 121c, in many cases, includes an electric circuit that amplifies the signals detected in the detecting section 121b, or performs analog-to-digital conversion. The electric signal generated by the signal processing section 121c has a voltage (in other words, voltage proportional to acceleration) proportional to an amount of a change detected by the detecting section 121b. Such an electric signal is output from the output section 121d to the outside (in the case of the present embodiment, a control unit 101). Moreover, such an acceleration sensor 121 may include a driving mechanism 121e for causing the movable section 121a to be driven in the case of having a servo mechanism, a self-diagnosis section 121f for performing functional diagnosis of the detecting section 121b, the environment correcting section 121g for performing temperature correction for a detected amount of displacement or a detected amount of strain at the time of performing conversion processing to electric signals by the signal processing section 121c, and the like.

In the above, while referring to FIG. 2A through FIG. 3, the endoscope unit 103 according to the present embodiment has been described in detail.

<With Regard to Constitution of Light Source Unit>

Successively, a constitution of the light source unit 105 according to the present embodiment is described in detail. In the case where the endoscope unit 103 according to the present embodiment includes a mechanism for making the radiation angle of illumination light changeable as having described previously, the light source unit 105 according to the present embodiment is not limited specifically, and it is possible to use publicly-known light source units. However, in the case where the endoscope unit 103 according to the present embodiment does not have a mechanism for making the radiation angle of illumination light changeable as having described previously, the light source unit 105 according to the present embodiment is required to be a light source unit capable of making the radiation angle of illumination light changeable. In that case, as a light source unit for making the radiation angle of illumination light changeable, for example, it is preferable to be one that includes a constitution as described in detail in the below.

Figure 4:
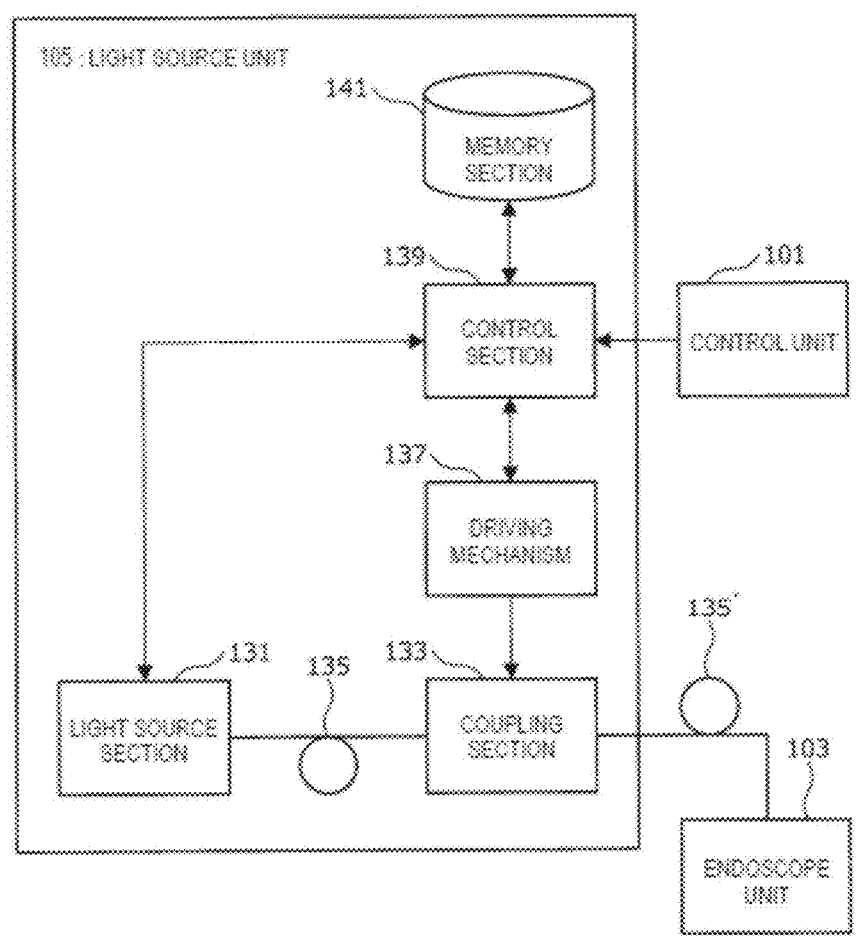
FIG. 4 is an explanatory diagram showing schematically one example of a constitution of a light source unit included by an endoscope apparatus according to the embodiment.
Figure 5:
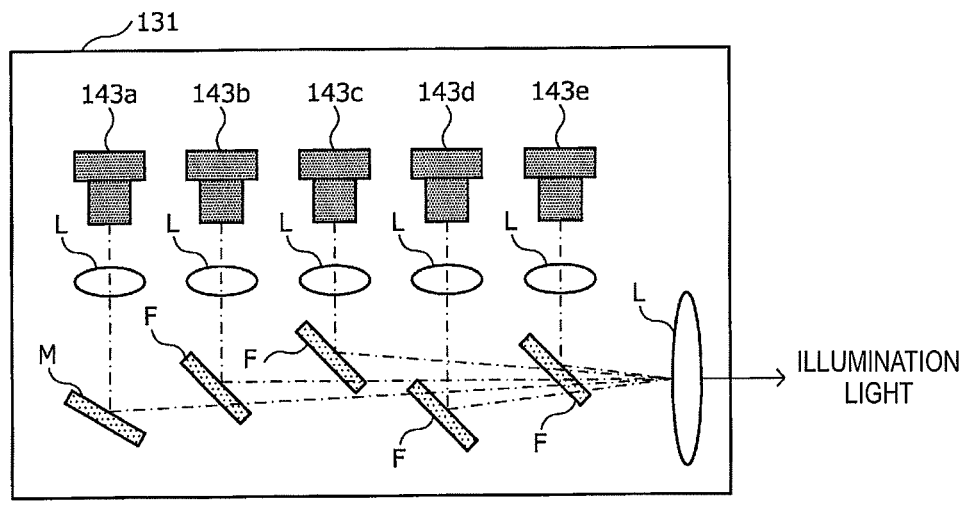
FIG. 5 is an explanatory diagram showing schematically one example of a light source section included by a light source unit according to the embodiment.
Figure 6A:
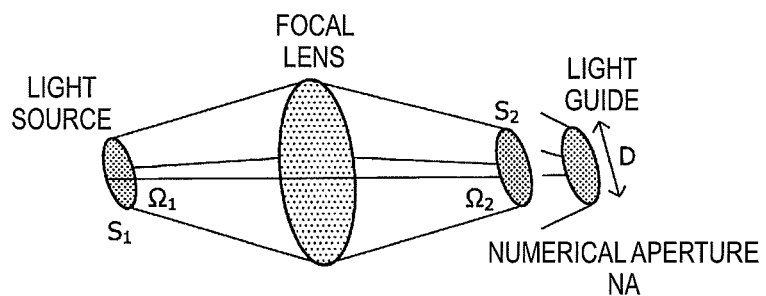
FIG. 6A is an explanatory illustration for describing Etendue.
Figure 6B:
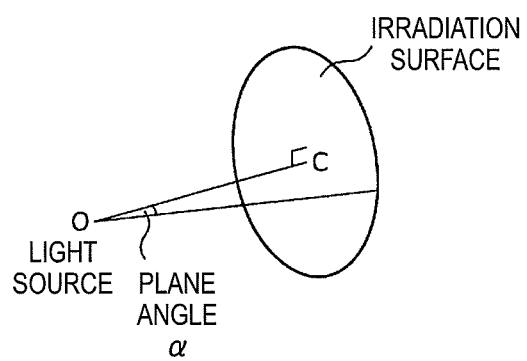
FIG. 6B is an explanatory illustration for describing Etendue.
Figure 7:
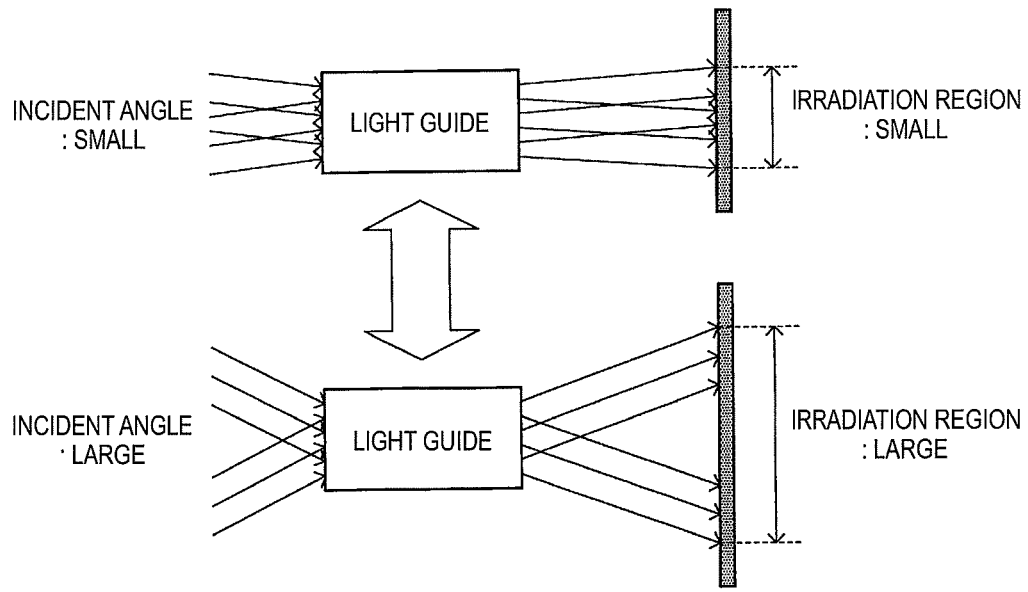
FIG. 7 is an explanatory illustration for describing control processing of an incident angle of illumination light to a light guide in a light source unit according to the embodiment.
Figure 8A:
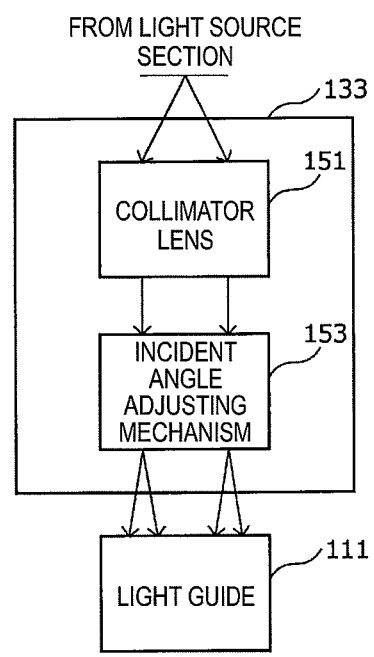
FIG. 8A is an explanatory diagram showing schematically a constitution of a coupling section included by a light source unit according to the embodiment.
Figure 8B:
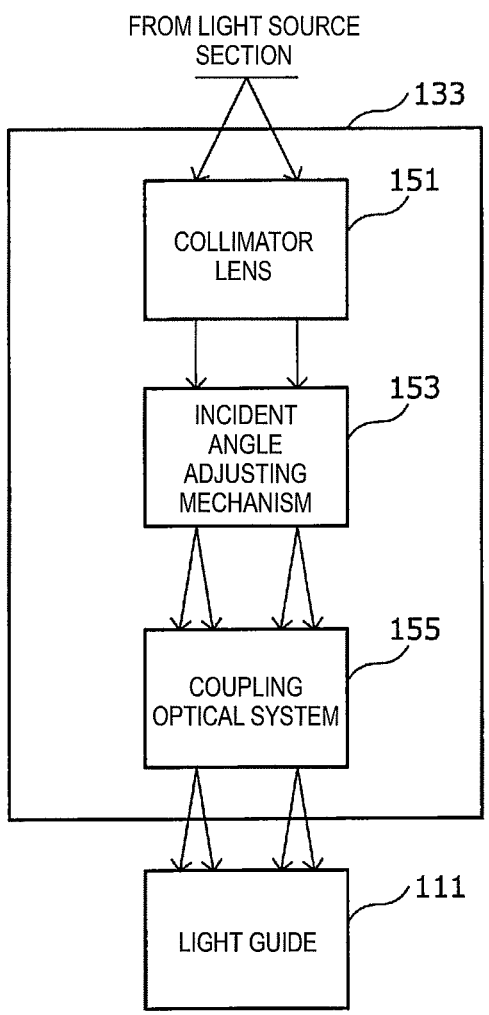
FIG. 8B is an explanatory diagram showing schematically a constitution of a coupling section included by a light source unit according to the embodiment.
Figure 8C:
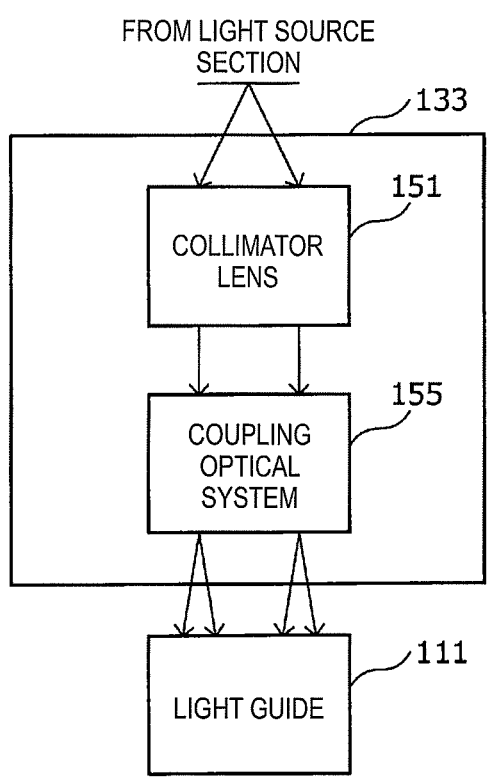
FIG. 8C is an explanatory diagram showing schematically a constitution of a coupling section included by a light source unit according to the embodiment.
Figure 9:
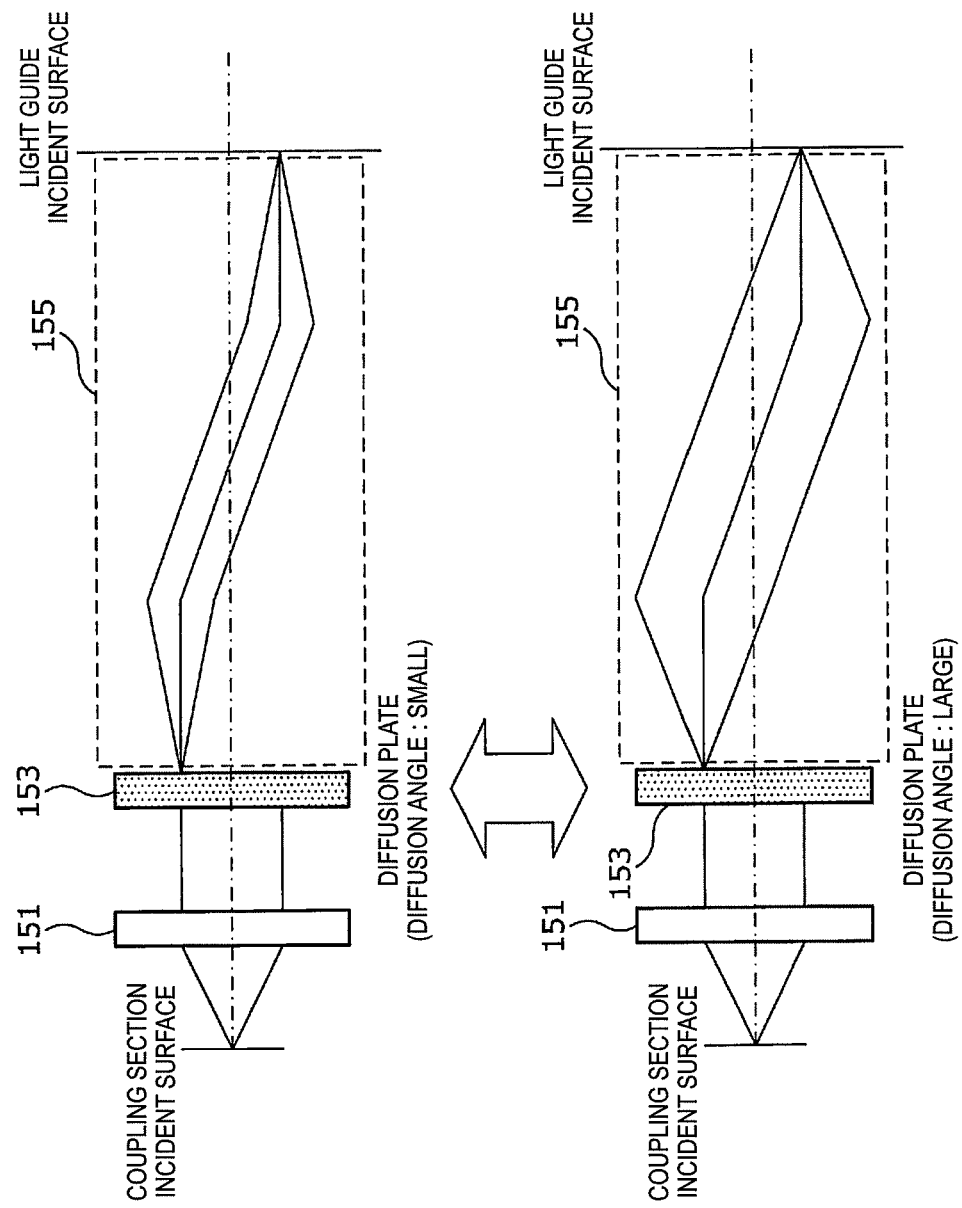
FIG. 9 is an explanatory illustration showing schematically the first concrete example of the coupling section according to the embodiment.
Figure 10:
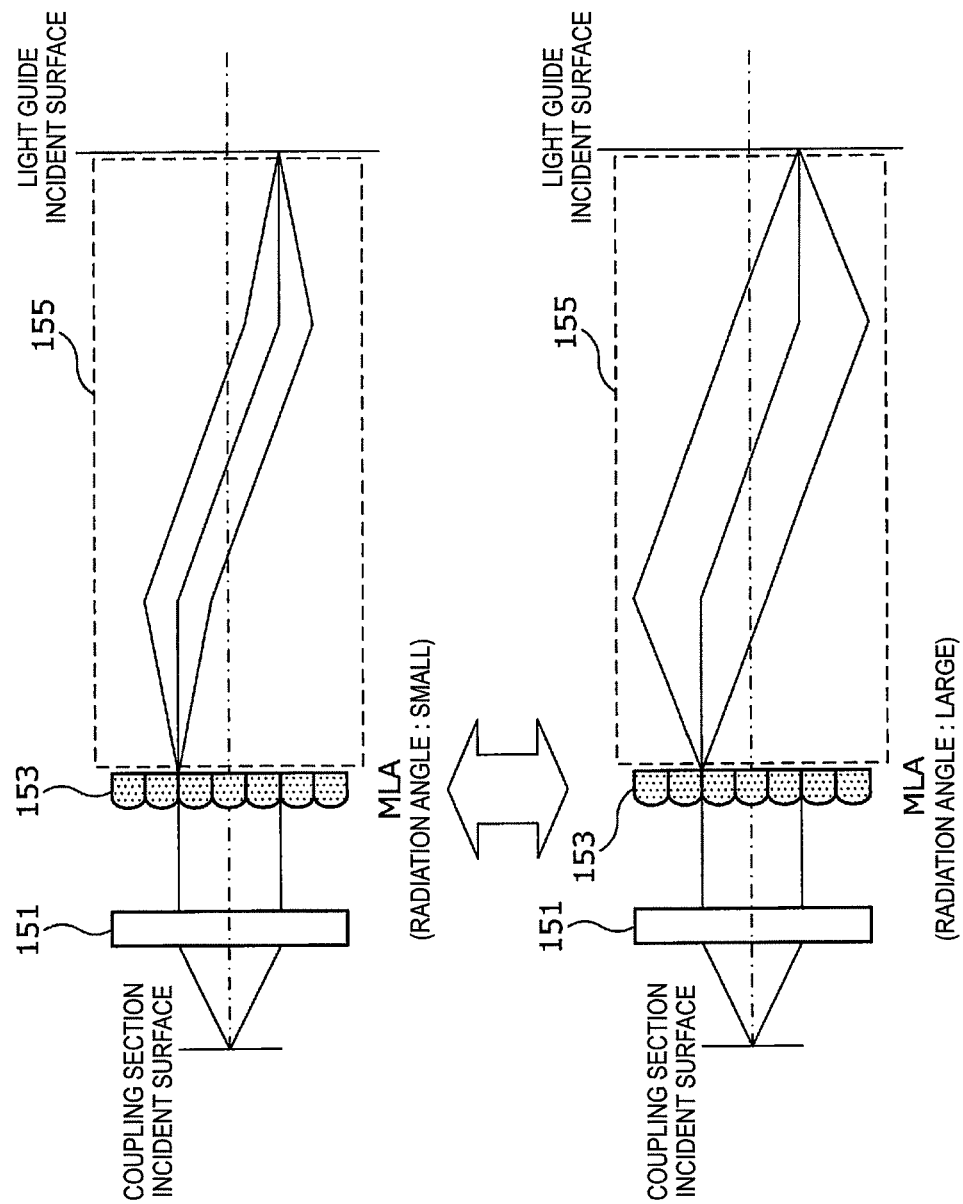
FIG. 10 is an explanatory illustration showing schematically the second concrete example of the coupling section according to the embodiment.
Figure 11:
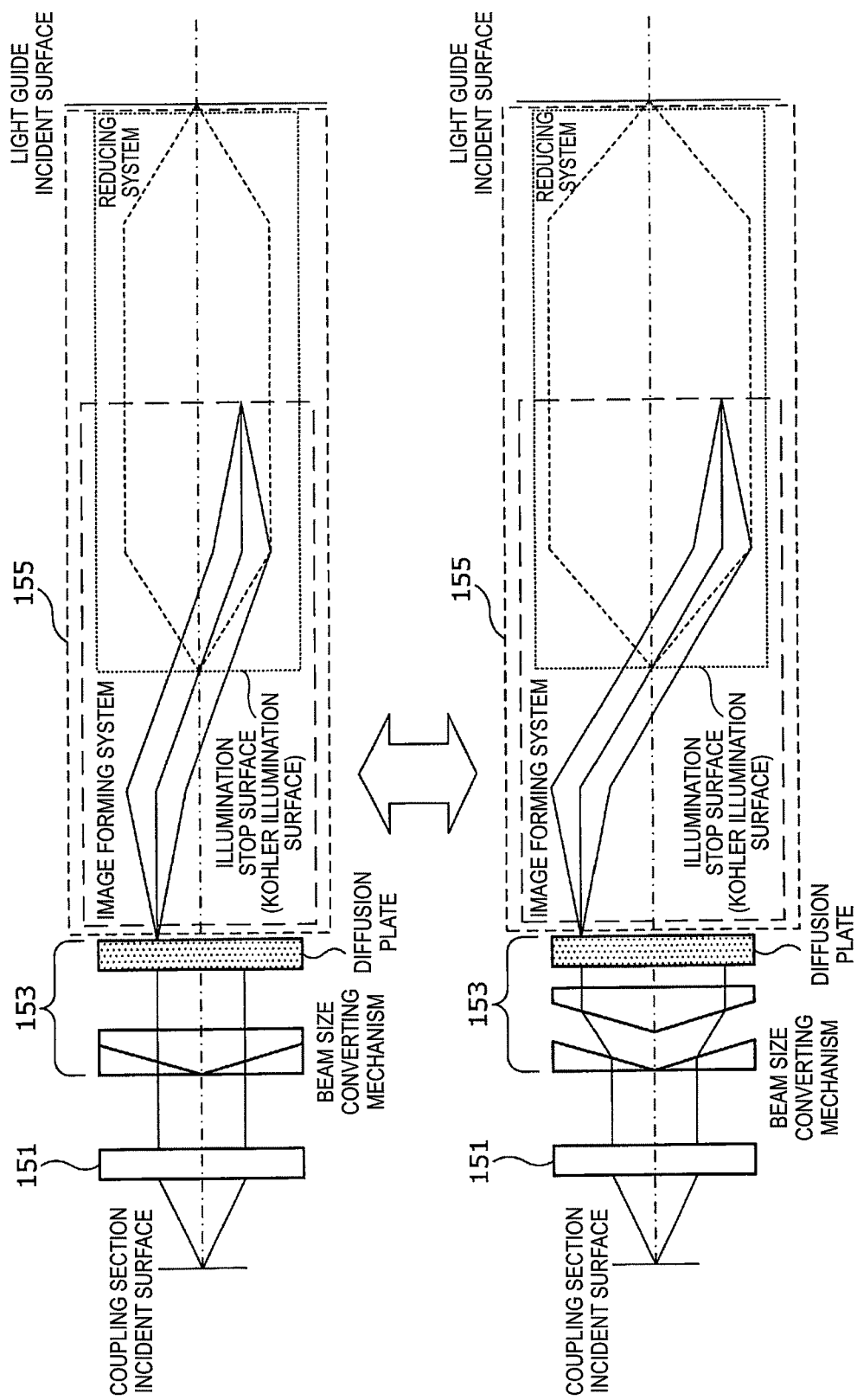
FIG. 11 is an explanatory illustration showing schematically the third concrete example of the coupling section according to the embodiment.
Figure 13:
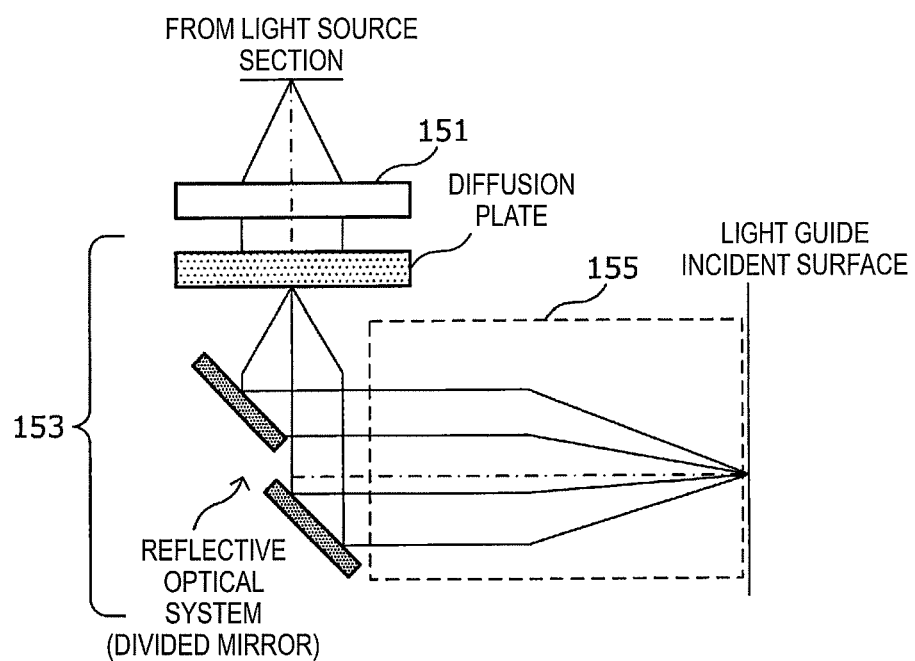
FIG. 13 is an explanatory illustration showing schematically the fifth concrete example of the coupling section according to the embodiment.

In the below, while referring to FIG. 4 through FIG. 15B, a light source unit capable of making the radiation angle of illumination light changeable is described concretely. FIG. 4 is an explanatory diagram showing schematically one example of a constitution of the light source unit included by the endoscope apparatus according to the present embodiment, and FIG. 5 is an explanatory diagram showing schematically one example of a light source section included by the light source unit according to the present embodiment. FIG. 6A and FIG. 6B each is an explanatory illustration for describing Etendue. FIG. 7 is an explanatory illustration for describing control processing of an incident angle of illumination light to a light guide in the light source unit according to the present embodiment. FIG. 8A through FIG. 8C each is an explanatory illustration showing schematically a constitution of a coupling section included by the light source unit according to the present embodiment. FIG. 9 is an explanatory illustration showing schematically a first concrete example of a coupling section according to the present embodiment, and FIG. 10 is an explanatory illustration showing schematically a second concrete example of a coupling section according to the present embodiment. FIG. 11 is an explanatory illustration showing schematically a third concrete example of a coupling section according to the present embodiment, and FIG. 12 is an explanatory illustration showing schematically a fourth concrete example of a coupling section according to the present embodiment. FIG. 13 is an explanatory illustration showing schematically a fifth concrete example of a coupling section according to the embodiment, and FIG. 14 through FIG. 15B each is an explanatory illustration showing schematically a sixth concrete example of a coupling section according to the present embodiment.

The light source unit 105 capable of making the radiation angle of illumination light changeable, mainly includes, as schematically shown in FIG. 4, a light source section 131, a multi-mode optical fiber 135, a coupling section 133, a multi-mode optical fiber 135', a driving mechanism 137, a control section 139, and a memory section 141.

The light source section 131 includes at least one or more solid light sources, and, emits light from such a solid light source as illumination light. Moreover, in the case where the light source section 131 includes two or more solid light sources, the light source section 131 can also emit white light by mixing the colors of light from the respective solid light sources. A detailed constitution of this light source section 131 will be described again below. The illumination light emitted from the light source section 131 is guided to the coupling section 133 mentioned later.

The coupling section 133 is a section to be connected to a light guide 111 that is disposed in the endoscope unit 103 and propagates a light flux (i.e., a light flux of illumination light) for connecting to the endoscope unit 103, and, is disposed to be able to be connected to such a light guide 111. The illumination light emitted from the light source section 131 is guided to the inside of the endoscope unit 103 through this coupling section 133. Moreover, in the light source unit 105 according to the present embodiment, as mentioned below in detail, this coupling section 133 is made to function as a center, whereby the incident angle of illumination light entering the light guide 111 is controlled. The detailed constitution of this coupling section 133 will be described below again.

The multi-mode optical fiber 135 is a multi-mode optical fiber having a core diameter of 10 μm or more, and, guides illumination light emitted from the light source section 131 to the coupling section 133. By connecting the light source section 131 and the coupling section 133 using the multi-mode optical fiber 135, it becomes possible to guide illumination light emitted from the light source section 131 to the coupling section 133 efficiently, and it becomes easy to handle the illumination light.

In this connection, as shown in FIG. 4, illumination light of the light source unit 105 is connected with the light guide 111 of the endoscope unit 103 in the coupling section 133 via the multi-mode optical fiber 135'. By a coupling optical system existing in such a coupling section 133, illumination light is guided to the light guide 111 of the endoscope unit 103.

The driving mechanism 137 is realized by publicly-known driving members, such as an actuator and a moving stage. The driving mechanism 137 sets the incident angle of light rays (i.e., light rays of illumination light) that enter the light guide 111 of the endoscope unit 103 in the coupling section 133, so as to become a proper value by controlling an incident-angle adjusting mechanism disposed in the coupling section 133 as described in detail in the below under the control of the control section 139 to be described in detail in the below.

The control section 139 is realized by various kinds of IC chips including, for example, a CPU, a ROM, a RAM, and so on. The control section 139 is a processing section that totally controls the operation of the light source unit 105 according to the present embodiment, and manages under the control of the control unit 101, for example, an emitting process of illumination light from the light source section 131, a control process of the coupling section 133 by the driving mechanism 137, and so on. With this, it becomes possible for the control section 139 to control such that the incident angle of light rays that enter the light guide 111 in the coupling section 133, becomes changeable.

In more details, the control section 139 outputs a predetermined control signal to the light source section 131, thereby causing illumination light to be emitted from the light source section 131.

In this connection, at the time of executing various kinds of control processes, it is possible for the control section 139 to use various kinds of parameters, a data base, various kinds of programs, etc. that are stored in the memory section 141. Moreover, the control section 139 may control the incident angle of light rays that enter the light guide 111 in the coupling section 133, under the control of the control unit 101, in accordance with various kinds of user's operations executed by an operator of the endoscope apparatus 10.

The memory section 141 is realized by, for example, a ROM, a RAM, a storage device, and so on. In the memory section 141, various kinds of parameters, a data base, various kinds of programs, etc. are stored that are able to be referred when the control section 139 executes various kinds of control processes. Moreover, in this memory section 141, temporary data, various kinds of history information, etc. may be stored that are created when the control section 139 executes various kinds of control processes. For this memory section 141, it is possible for the control section 139 to execute reading/writing processes of data freely.

In the above, the detailed entire constitution of the light source unit 105 according to the present embodiment has been described while referring to FIG. 4.

[With Regard to Constitution of Light Source Section 131]

Next, one example of a constitution of the light source section 131 included in the light source unit 105 according to the present embodiment is described in detail while referring to FIG. 5 to FIG. 6B.

In the case where illumination light having a wavelength that belongs to a visible light band is used as illumination light, it is preferable that, for example as shown in FIG. 5, the light source section 131 according to the present embodiment includes a plurality of solid light sources 143a, 143b, 143c, 143d, 143e • • • (hereinafter, collectively referred to also as a solid light source 143). From each of the solid light sources 143, light of a prescribed wavelength is emitted. Here, a combination of the wavelengths of light emitted from each of the solid light sources 143 is not limited specifically. However, as a result of mixing the colors of light emitted from each of the solid light sources 143, a combination capable of obtaining white light is preferable. As a combination of such wavelengths, it is preferable that, for example, any one of the solid light sources 143a to 143e emits red light, any one of the solid light sources 143a to 143e emits a green light, and any one of the solid light sources 143a to 143e emits blue light. Moreover, any one of the solid light sources 143a to 143e may emit purple light or yellow light, and any one of the solid light sources 143a to 143e may emit infrared light.

The propagating direction of light emitted from each of the solid light sources 143 is controlled by a lens L, a mirror M, and an optical filter F disposed at a stage following each of the solid light sources 143, and is finally relayed to the next optical system by a lens L disposed at a stage following the mirror M and the optical filter F. Here, the mirror M has an optical property to reflect light emitted from the solid light source 143a, and each of the optical filters F has an optical property that reflects light emitted from a solid light source 143 disposed at an upstream side of each of the optical filters F and allows light having wavelength bands other than it to pass through. The light after having been subjected to color mixture is emitted to the outside of the light source section 131 as illumination light.

Here, while referring to FIG. 6A to FIG. 6B, the relationship between the Etendue of the solid light source 143 and the Etendue of the light guide 111 of the endoscope unit 103 is described concretely.

Etendue is another representation of Helmholtz-Lagrange's conservation law, and, is expressed by the product of a light emitting area and the solid angle of light rays. Now, as shown in FIG. 6A, it is assumed that the light emitting area of a light source and the solid angle of light emitted from the light source are denoted as $S_1$ and $\Omega_1$ respectively, and the area of an incident surface of the light guide 111 and the solid angle of light that enters the incident surface, are denoted as $S_2$ and $\Omega_2$ respectively. At this time, since the value of Etendue is conserved in the optical system to be noticed, Formula 101 shown below is established. Here, the unit of the Etendue becomes [mm$^2$·sr] (square millimeter·steradian) in the case of using an $S_1$ unit system.

Moreover, in the case where light is radiated in rotation symmetry relative to an optical axis C, a solid angle [unit: sr] can be expressed by Formula 103 shown below in the case of using a plane angle $\alpha$ [unit: rad] as shown in FIG. 6B, and the numerical aperture NA of a light guide can be expressed by Formula 105 shown below by using the plane angle $\alpha$. Therefore, Formula 101 that gives the value of Etendue can be expressed by Formula 107 shown below by using Formula 103 and Formula 105 shown below. Here, in Formula 107 shown below, D represents a diameter of a light guide.

[Math. 1]

$$S_1 \cdot \Omega_1 = S_2 \cdot \Omega_2 \quad \text{(Formula 101)}$$

$$\Omega = 2\pi(1 - \cos \alpha) \quad \text{(Formula 103)}$$

$$NA = \sin \alpha \quad \text{(Formula 105)}$$

$$S_1 \cdot \Omega_1 = S_2 \cdot \Omega_2 = \pi\left(\frac{D}{2}\right)^2 \cdot 2\pi\left(1 - \sqrt{1 - (NA)^2}\right) \quad \text{(Formula 107)}$$

If generalizing, Etendue (hereinafter, its value is denoted as E) can be expressed by Formula 109 shown below by using the radiation angle distribution I ($\theta$, $\varphi$) ($\theta$, $\varphi$: a radiation angle of light rays) of the intensity of light rays emitted from a light source. Here, it is assumed that a light source to be noticed is a Lambertian (Lambertian) light source, the radiation angle distribution I ($\theta$, $\varphi$) of the intensity can be expressed by Formula 111 shown below by using the intensity $I_0$. In that case, Etendue becomes like Formulas 113 shown below. On the other hand, since the relation of Formula 115 shown below is established, the Etendue of the Lambertian light source becomes smaller than that of a light source having no radiation angle distribution.

[Math. 2]

$$E = S \cdot \Omega = S \int I(\theta, \phi) d\Omega \quad \text{(Formula 109)}$$

$$I(\theta, \phi) = I_0 \cdot \cos \theta \quad \text{(Formula 111)}$$

$$E = S \cdot I_0 \cdot \pi (1 - \cos^2 \theta) = SI_0\pi(NA)^2 \quad \text{(Formula 113)}$$

$$\pi(NA)^2 < 2\pi\sqrt{1 - (NA)^2} = \quad \text{(Formula 115)}$$
$$2\pi\left(\frac{(NA)^2}{2} + \frac{(NA)^4}{8} + \frac{(NA)^6}{16} + \cdots\right)$$

Here, in the case where the Etendue of a light guide with a common diameter D and numerical aperture NA is calculated on the presupposition that the radiation angle distribution I ($\theta$, $\varphi$) of intensity is uniform at $I_0$, it becomes clear as below. That is, it becomes clear that with regard to the light from a light source with the Etendue larger than the Etendue, all of it cannot be coupled to a light guide. On the other hand, with regard to the light from a light source with the Etendue smaller than the Etendue, all of it can be coupled to a light guide.

Therefore, it is preferable that the solid light sources 143 used in the light source section 131 according to the present embodiment is a light source having the Etendue equal to or less than the Etendue of the light guide 111. By using such a solid light source, it becomes possible to use all of light emitted from the solid light source, and it is possible to improve the utilization efficiency of the light source.

In such a viewpoint, it turns out that, since a light emitting point is very small, a light source preferable as a solid light source is a laser light source (for example, semiconductor laser light source) that can emit parallel light (that is, a solid angle becomes almost zero) easily by an optical system. Moreover, it is also possible to use a laser excitation phosphor light source in which such a laser light source is used as an excitation light source for a phosphor.

Moreover, although the development of a light emitting diode (Light Emitting Diode: LED) element is also active in recent years, since light emission in the LED elements is surface light emission, a light emitting region becomes large. Accordingly, the value of Etendue becomes larger than that of the laser light source. However, depending on its performance, it is possible to use it as the solid light source according to the present embodiment.

In the above, while referring to FIG. 5 to FIG. 6B, one example of the light source section 131 according to the present embodiment has been described in detail. In this connection, the constitution of the light source section 131 shown in FIG. 5 is merely one example, and the constitution of the light source section 131 according to the present embodiment should not be limited to one shown in FIG. 5.

[With Regard to Constitution of Coupling Section 133]

Next, while referring to FIG. 7 to FIG. 15B, a constitution of the coupling section 133 included in the light source unit 105 according to the present embodiment is described in detail.

As a result of having studied earnestly a light source unit capable of making the area of a region irradiated with illumination light changeable, the present inventors have obtained the knowledge that it is possible to control the radiation angle of light rays emitted from a light guide by changing the incident angle (angle formed by incident light rays relative to the optical axis of a light guide) of light rays that enter the light guide.

Namely, as shown schematically in FIG. 7, in the case where light rays enter at a small incident angle relatively to a light guide, the radiation angle of the light rays emitted from the light guide becomes a small value (at the upper stage in FIG. 7). In the case where light rays enter at a large incident angle relatively to the light guide, the radiation angle of the light rays emitted from the light guide becomes a large value (at the lower stage in FIG. 7). The reasons are that a general light guide is those in which a plurality of index guide type multi-mode optical fibers with a core diameter of about 10 μm to 80 μm is bundled (bundled) and that the optical fiber has the characteristics to radiate light rays from an emitting end surface while keeping the angle of the light rays having entered an incident end surface. However, in the optical fiber, although the incident angle of light rays is preserved, the incident position of the light rays is not preserved. Accordingly, the light rays having entered at a certain incident angle become ring-shaped light rays while keeping the angle, and then, are radiated from the emitting end surface.

As shown schematically at an upper stage in FIG. 7, with this phenomenon, by making the incident angle of light rays to the light guide relatively small, the radiation angle of the light rays from the light guide becomes small. As a result, it becomes possible to narrow the irradiation region of the light rays radiated from the light guide to small. On the contrary, as shown schematically at a lower stage in FIG. 7, by making the incident angle of light rays to the light guide relatively large, the radiation angle of the light rays from the light guide becomes large. As a result, it becomes possible to greatly expand the irradiation region of the light rays radiated from the light guide.

In the coupling section 133 according to the present embodiment, the incident angle of light rays to the light guide 111 is controlled as described in the above, thereby controlling the radiation angle of the light rays introduced to the light guide and making the area of a region irradiated with illumination light changeable.

Here, the coupling section 133 may control the incident angle of light rays that enter a light guide, to two kinds of incident angles, for example, an incident angle close to parallel light and an incident angle close to the numerical aperture NA of the light guide, or, may control the incident angles from an incident angle close to parallel light to an incident angle close to the numerical aperture NA of the light guide to multi stages.

It is preferable that the coupling section 133 having such a function includes at least a collimator lens 151 and an incident angle adjusting mechanism 153 as shown in FIG. 8A. The collimator lens 151 is an optical element that makes illumination light that has entered the coupling section 133 from the light source section 131, to parallel light. Moreover, the incident angle adjusting mechanism 153 is a mechanism that adjusts the incident angle of illumination light to the light guide as having described while referring to FIG. 7. As the driving mechanism 137 shown in FIG. 4 functions, the state of the incident angle adjusting mechanism 153 changes so as to change, for example, the beam size or divergent angle of the light having entered the coupling section 133, whereby the incident angle adjusting mechanism 153 changes the incident angle of the illumination light to the light guide 111. A concrete example of this incident angle adjusting mechanism 153 will be described again in the below.

Moreover, it is preferable that the coupling section 133 according to the present embodiment further includes a coupling optical system 155 at the stage following the incident angle adjusting mechanism 153 as shown in FIG. 8B. The coupling optical system 155 is an optical system that couples light rays whose incident angle to the light guide has been controlled, to the light guide 111 of the endoscope unit 103. By providing such an optical system, it becomes possible to couple illumination light whose incident angle to the light guide 111 has been controlled, to the light guide 111 more certainly. As such an optical system, it is possible to apply a publicly-known optical system such as a fixed magnification optical system as long as it does not change the controlled incident angle of the illumination light.

Moreover, as shown in FIG. 8C, in the coupling section 133 according to the present embodiment, the coupling optical system 155 may also have the function of the incident angle adjusting mechanism 153. That is, by changing the magnification of the coupling optical system 155, it becomes possible to change the beam size of illumination light on the incident surface of the light guide 111. Owing to such a change of the beam size, since the incident angle of illumination light on the incident surface of the light guide 111 changes, it becomes possible to realize the control of an illumination region as having described with reference to FIG. 7.

In the case of performing the control of the area of an illumination region and narrowing the illumination region in this way, an amount of illumination light having dispersed to a wide area before the changing, is concentrated to the narrowed illumination region after the changing. As a result, it becomes possible to make the illumination region brighter, and, in addition, it becomes possible to use the illumination light more efficiently.

First Concrete Example of Coupling Section 103

The first concrete example of the coupling section 133 having the above-described functions is described while referring to FIG. 9.

In the first concrete example of the coupling section 133 shown in FIG. 9, a diffusion plate is used as the incident angle adjusting mechanism 153. By using the diffusion plate as the incident angle adjusting mechanism 153, it is possible to change the divergent angle of light rays (i.e., illumination light) that enter the diffusion plate, and, with this, it is possible to change the incident angle of light rays to the light guide 111.

Namely, in the coupling section 133 in the first concrete example, the diffusion plate is disposed as the incident angle adjusting mechanism 153 at the stage following the collimator lens 151, and the fixed magnification optical system as one example of the coupling optical system 155 is disposed at the stage following the diffusion plate. In this case, as shown at an upper stage in FIG. 9, in the case where a diffusion plate with a small diffusion angle is disposed on the optical path, the incident angle of illumination light on the incident surface of the light guide 111 becomes a relatively small angle, and the irradiation region of the illumination light becomes narrow relatively. On the other hand, as shown at a lower stage in FIG. 9, in the case where a diffusion plate with a large diffusion angle is disposed on the optical path, the incident angle of the illumination light on the incident surface of the light guide 111 becomes a relatively large angle, and the irradiation region of the illumination light becomes wide relatively.

Therefore, in the coupling section 133, by preparing a plurality of diffusion plates different in diffusion angle, and by replacing the diffusion plate to be disposed on the optical path with the driving mechanism 137, it becomes possible to realize the above functions. In this connection, not only by replacing the plurality of diffusion plates different in diffusion angle, but also, by increasing or decreasing the number of diffusion plates to be disposed on the optical path, it is possible to obtain the effects similar to the above.

Second Concrete Example of Coupling Section 133

Next, the second concrete example of the coupling section 133 is described while referring to FIG. 10. In the first concrete example, as the incident angle adjusting mechanism 153, the diffusion plate is disposed. However, in the second concrete example, as the incident angle adjusting mechanism 153, a multi lens array (Multi Lens Array: MLA) in which a plurality of lenses is arranged in an array form, is disposed. By changing the focal length of the multi lens array to be disposed on the optical path, it is possible to change the divergent angle of light rays (i.e., illumination light) that enter the multi lens array. With this, it is possible to change the incident angle of light rays to the light guide 111.

That is, in the coupling section 133 in the second concrete example, the multi lens array is disposed at the stage following the collimator lens 151 as the incident angle adjusting mechanism 153, and a fixed magnification optical system is disposed at the stage following the multi lens array as an example of the coupling optical system 155. As shown at an upper stage in FIG. 10, in the case where a multi lens array with a long focal length is disposed on the optical path, the incident angle of illumination light on the incident surface of the light guide 111 becomes a relatively small angle, and the irradiation region of illumination light becomes narrow relatively. On the other hand, as shown at a lower stage in FIG. 10, in the case where a multi lens array with a short focal length is disposed on the optical path, the incident angle of illumination light on the incident surface of the light guide 111 becomes a relatively large angle, and the irradiation region of illumination light becomes wide relatively.

Therefore, in the coupling section 133, by preparing a plurality of multi lens arrays different in focal length, and by replacing the multi lens array to be disposed on the optical path with the driving mechanism 137, it becomes possible to realize the function like the above. In this connection, not only by replacing the plurality of multi lens arrays different in focal length, but also, by increasing or decreasing the number of multi lens arrays to be disposed on the optical path, it is possible to obtain the effects similar to the above.

Third Concrete Example of Coupling Section 133

Next, the third concrete example of the coupling section 133 is described while referring to FIG. 11.

In the third concrete example, as the incident angle adjusting mechanism 153, a beam size converting mechanism capable of being separated into a lens with a conical surface and a lens with a concave surface corresponding to the conical surface and a diffusion plate are disposed. This beam size converting mechanism can convert the beam size of entering illumination light by separating the two lenses and changing the distance between the two lenses. That is, in the case where the two lenses are united, the beam size of the entering illumination light is maintained as it was in the state of having entered. On the other hand, in the case where the lens with the conical surface is separated away, it becomes possible to convert the beam size of the entering illumination light to a large size. Therefore, it can be said that this beam size converting mechanism is an optical element capable of creating a virtual light surface optically. By making illumination light having passed through the beam size converting mechanism further diffuse by a diffusion plate, and by coupling it to the incident surface of the light guide 111 by the coupling optical system (in this case, the coupling optical system includes a fixed magnification optical system and a reducing optical system) disposed at the stage following the diffusion plate, it is possible to make the incident angle of light rays to the light guide 111 change.

That is, in the coupling section 133 in the third concrete example, as shown at an upper stage in FIG. 11, in the case where the beam size converting mechanism is not separated to two pieces, the incident angle of illumination light on the incident surface of the light guide 111 becomes a relatively small angle, and the irradiation region of illumination light becomes narrow relatively. On the other hand, as shown at a lower stage in FIG. 11, in the case where the beam size converting mechanism is separated into two pieces, the incident angle of illumination light on the incident surface of the light guide 111 becomes a relatively large angle, and the irradiation region of illumination light becomes wide relatively.

Therefore, in the coupling section 133, by controlling the separation state of the beam size converting mechanism by the driving mechanism 137, it becomes possible to realize the function like the above.

Fourth Concrete Example of Coupling Section 133

Next, the fourth concrete example of the coupling section 133 is described while referring to FIG. 12. In the fourth concrete example, as the incident angle adjusting mechanism 153, a reflective optical system such as a mirror is disposed, and by controlling an incident position to the coupling optical system 155, it becomes possible to change the incident angle of light rays to the light guide 111.

Namely, as shown at an upper stage in FIG. 12, by controlling the position of the reflective optical system so as to control to make illumination light from the light source section 131 enter near the optical axis of the coupling optical system 155, the incident angle of the illumination light on the incident surface of the light guide 111 becomes a relatively small angle, and the irradiation region of the illumination light becomes narrow relatively. On the other hand, as shown at a lower stage in FIG. 12, by controlling the position of the reflective optical system so as to control to make illumination light from the light source section 131 enter a position away from the optical axis of the coupling optical system 155, the incident angle of the illumination light on the incident surface of the light guide 111 becomes a relatively large angle, and the irradiation region of the illumination light becomes wide relatively. In this connection, in the case shown at a lower stage in FIG. 12, illumination light enters the light guide 111 from a certain one direction. However, in the light guide 111 including a plurality of optical fibers, as described earlier, although an incident angle is preserved, an incident position is not preserved. Accordingly, illumination light having entered from one direction becomes to be diffracted over the entire circumference, whereby it becomes possible to illuminate the entirety of a desired region.

Therefore, in the coupling section 133, by controlling the position of the reflective optical system such as a mirror by the driving mechanism 137, it becomes possible to realize the function like the above.

Fifth Concrete Example of Coupling Section 133

Next, the fifth concrete example of the coupling section 133 is described while referring to FIG. 13. In the fourth concrete example, as a control method of a mirror, only a simple transverse movement as shown in FIG. 12 has been described. However, by executing control, such as separating mirrors and then moving both the mirrors in the respective directions reverse to each other, or moving one of them in the radial direction, it becomes possible to control the incident angle variously similarly to the fourth concrete example. In the below, a concrete example where such mirrors are divided is described briefly.

In the present concrete example, as shown schematically in FIG. 13, as the incident angle adjusting mechanism 153, a reflective optical system such as divided mirrors (hereinafter, also merely referred to as "divided mirrors") is disposed. By moving at least any one of such divided mirrors, the incident angle of illumination light to the coupling optical system 155 is controlled, whereby the incident angle of light rays to the light guide 111 is changed.

In concreter terms, the reflective optical system which has been a single mirror in the fourth concrete example may be divided into two mirrors in which one of them is located on the sheet surface front side of a flat surface parallel to the sheet surface and the other one is located on the sheet surface back side. Alternatively, the reflective optical system which has been a single mirror in the fourth concrete example may be divided into two mirrors in which one of them is located on the sheet surface upper side of a flat surface vertical to the sheet surface and the other one is located on the sheet surface lower side. In addition to that, by making any one of divided mirrors move, it becomes possible to make the incident angle of illumination light on the incident surface of the light guide 111 change.

Therefore, in the coupling section 133, by controlling the position of the reflective optical systems, such as divided mirrors, with the driving mechanism 137, it becomes possible to realize the function like the above.

Sixth Concrete Example of Coupling Section 133

Figure 14:
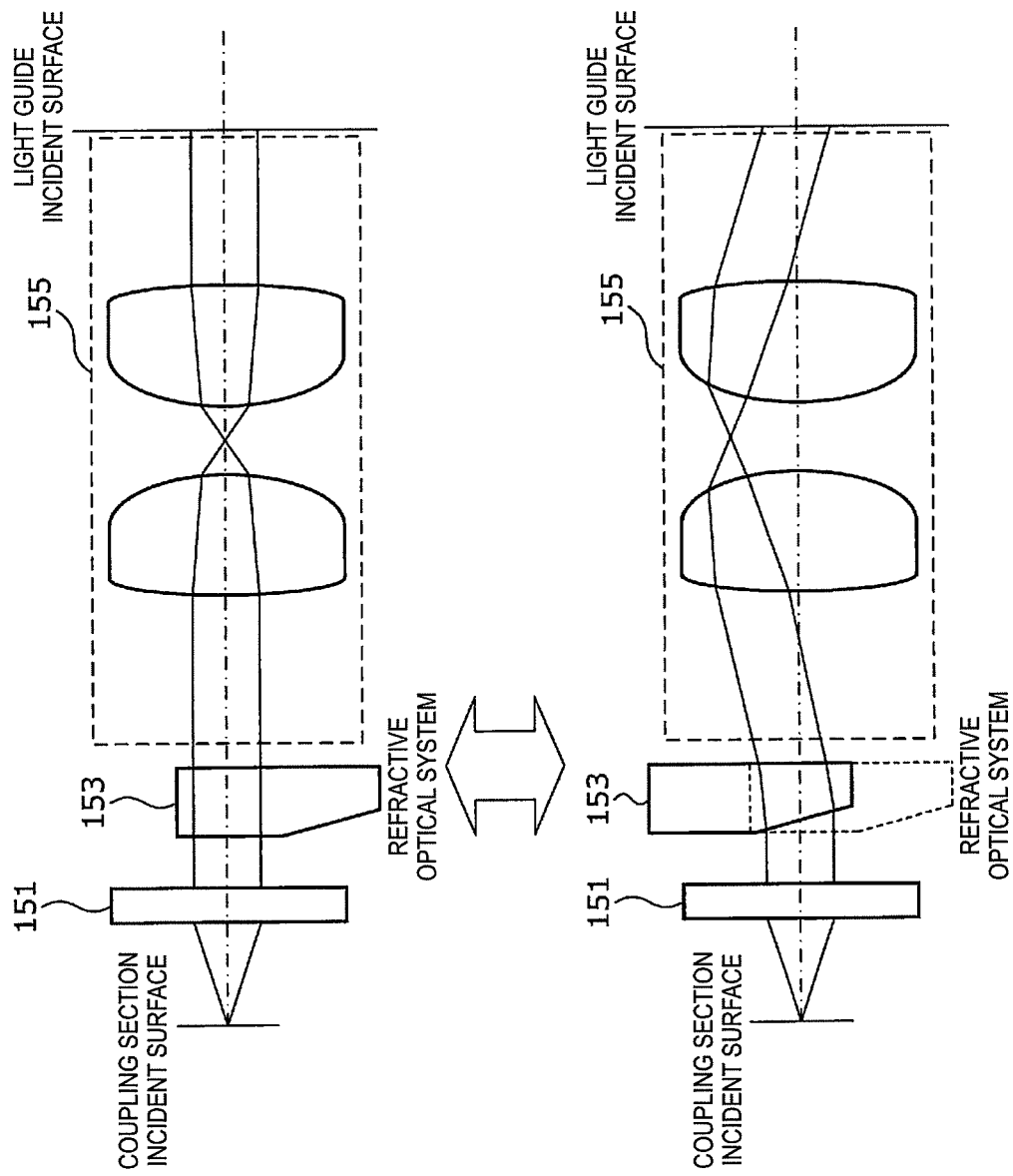
FIG. 14 is an explanatory illustration showing schematically the sixth concrete example of the coupling section according to the embodiment.
Figure 15A:
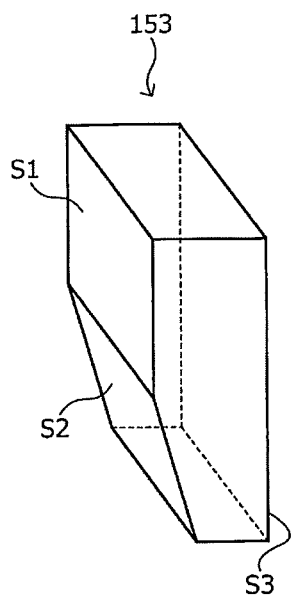
FIG. 15A is an explanatory illustration showing schematically the sixth concrete example of the coupling section according to the embodiment.
Figure 15B:
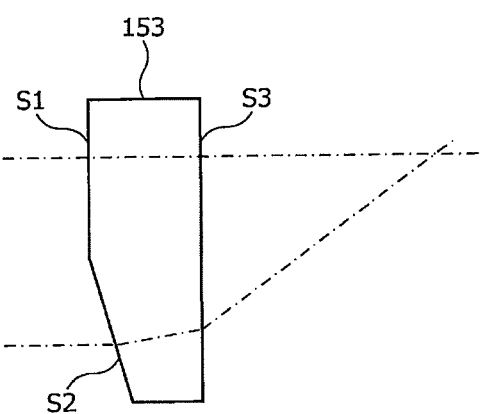
FIG. 15B is an explanatory illustration showing schematically the sixth concrete example of the coupling section according to the embodiment.

Next, the sixth concrete example of the coupling section 133 is described while referring to FIG. 14 to FIG. 15B. In the sixth concrete example, as shown schematically in FIG. 14, as the incident angle adjusting mechanism 153, a refractive optical system, such as a structure prism, is disposed. Accordingly, by controlling the incident angle of illumination light to the coupling optical system 155, it becomes possible to change the incident angle of light rays to the light guide 111.

One example of a structure of the structure prism is shown in FIG. 15A and FIG. 15B. The structure prism capable of being used as the incident angle adjusting mechanism 153 includes optically transmitting surfaces S1, S2, and S3 as shown in FIG. 15A and FIG. 15B. The optically transmitting surface S1 and the optically transmitting surface S3 are parallel to each other. Moreover, the optically transmitting surface S2 and the optically transmitting surface S3 are not parallel to each other, and the optically transmitting surface S2 forms an inclined surface with a predetermined angle. As shown in FIG. 15B, the optically transmitting surface S1 and the optically transmitting surface S3 are made vertical to the optical axis of the optical system in which this structure prism is disposed, the optical axis of light that enters the optically transmitting surface S1 and is emitted from the optically transmitting surface S3, is parallel to the optical axis of the optical system, and the advancing direction of the light does not change. However, since he optically transmitting surface S2 is inclined relative to the optical axis of the optical system in which this structure prism is disposed, the optical axis of light that enters the optically transmitting surface S2 and is emitted from the optically transmitting surface $S_3$, has an angle corresponding to the inclination angle of the optically transmitting surface $S_2$ due to the effect of refraction.

As shown at an upper stage in FIG. 14, by utilizing such a structure prism, by controlling the position of a refractive optical system (structure prism), and by controlling illumination light from the light source section 131 so as to enter in almost parallel to the optical axis of the coupling optical system 155, the incident angle of the illumination light on the incident surface of the light guide 111 becomes a relatively small angle, and the irradiation region of the illumination light becomes narrow relatively. On the other hand, as shown at a lower stage in FIG. 14, by controlling the position of the refractive optical system, and by controlling illumination light from the light source section 131 so as to enter with an angle to the optical axis of the coupling optical system 155, the incident angle of the illumination light on the incident surface of the light guide 111 becomes a relatively large angle, and the irradiation region of the illumination light becomes wide relatively.

In this connection, in the case shown at the lower stage in FIG. 14, illumination light enters the light guide 111 from a certain one direction. However, in the light guide 111 including a plurality of optical fibers, as described earlier, although an incident angle is preserved, an incident position is not preserved. Accordingly, illumination light having entered from one direction becomes to be diffracted over the entire circumference, whereby it becomes possible to illuminate the entirety of a desired region.

Therefore, in the coupling section 133, by controlling the position of the refractive optical system such as a structure mirror with the driving mechanism 137, it becomes possible to realize the function like the above.

In this connection, in the sixth concrete example, the refractive optical system such as a structure mirror is disposed between the collimator lens 151 and the coupling optical system 155. However, even if the refractive optical system, such as a structure prism, is disposed immediately before the incident surface of the light guide 111, the similar effect can be acquired.

Here, in the first to sixth concrete examples, the incident angle adjusting mechanism 153 is disposed and the incident angle of light rays to the light guide 111 is changed. However, by changing an angle formed by the optical axis of the light guide 111 in a coupled state and the optical axis of the coupling section 133, it is possible to change the incident angle of illumination light to the light guide 111.

Namely, in the case where the coupling section 133 is coupled to the light guide 111 such that the optical axis of the coupling section 133 and the optical axis of the light guide 111 are coincident with each other, the incident angle of illumination light on the incident surface of the light guide 111 becomes a relatively small angle, and the irradiation region of the illumination light becomes narrow relatively. On the other hand, in the case where the coupling section 133 is inclined obliquely relative to the light guide 111, the incident angle of illumination light on the incident surface of the light guide 111 becomes a relatively large angle, and the irradiation region of the illumination light becomes wide relatively.

Therefore, by controlling the inclined state of the coupling section 133 with the driving mechanism 137, it becomes possible to realize the function like the above.

In the above, while referring to FIG. 4 through FIG. 15B, the light source unit 105 capable of making the radiation angle of illumination light changeable has been described concretely.

<With Regard to Constitution of Control Unit>

Figure 16:
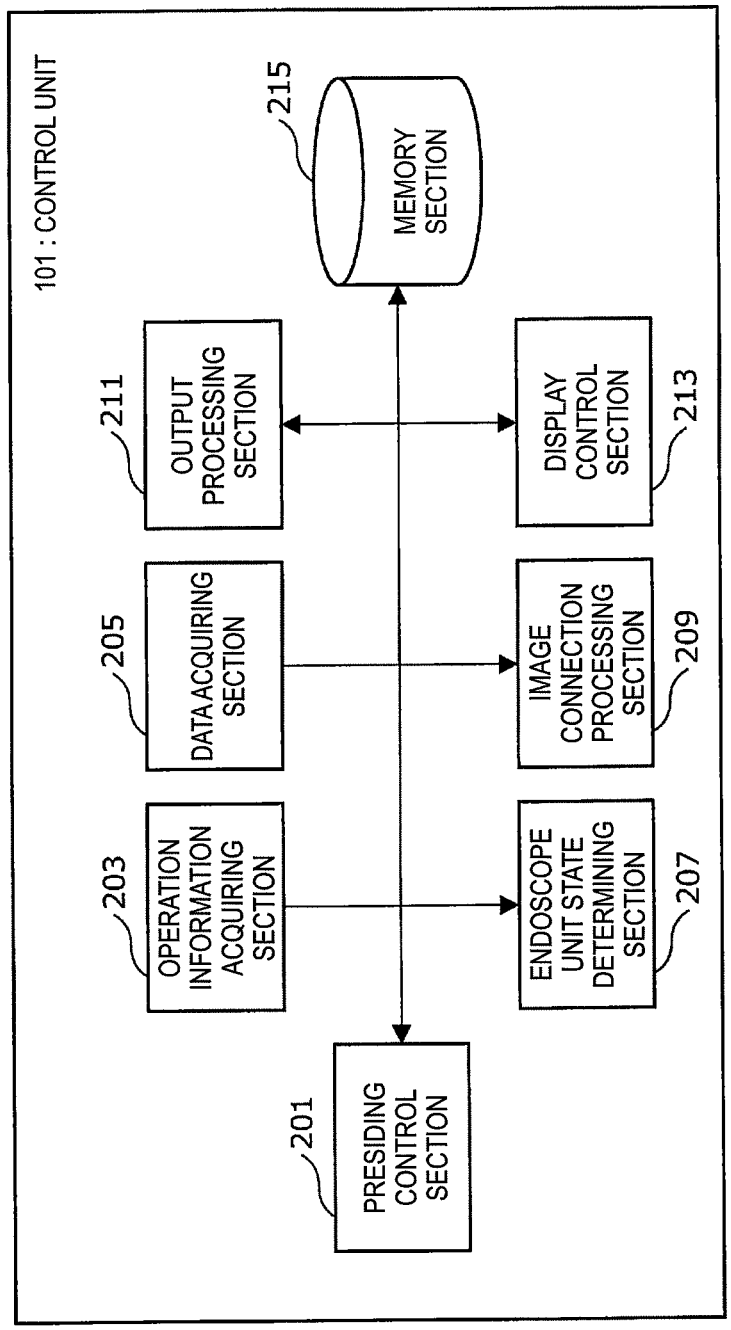
FIG. 16 is a block diagram showing schematically one example of a constitution of a control unit equipped by an endoscope apparatus according to the embodiment.
Figure 17:
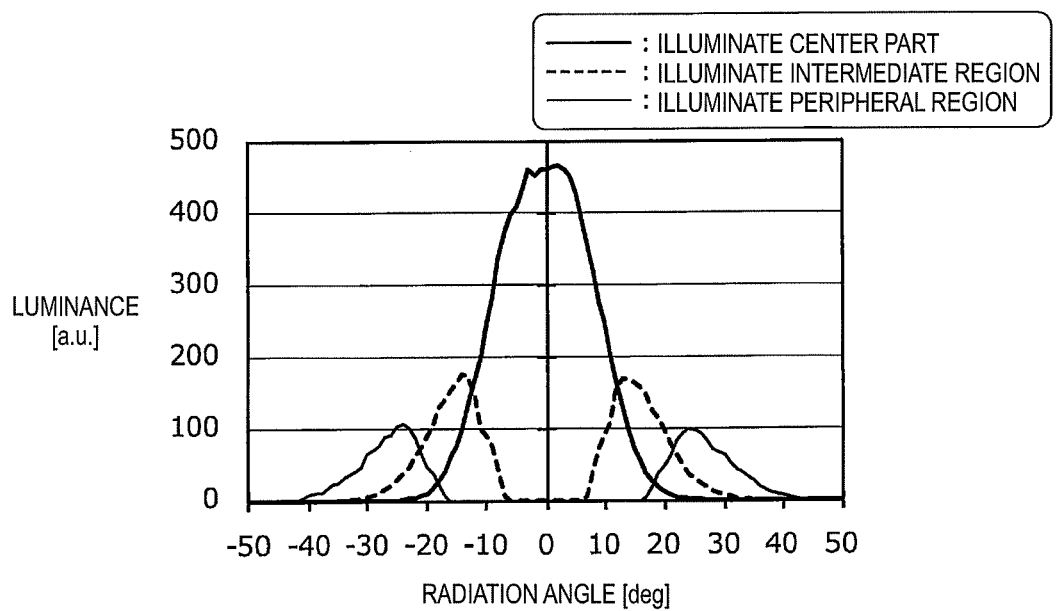
FIG. 17 is an explanatory diagram for describing illumination region control processing in a control unit according to the embodiment.
Figure 18:
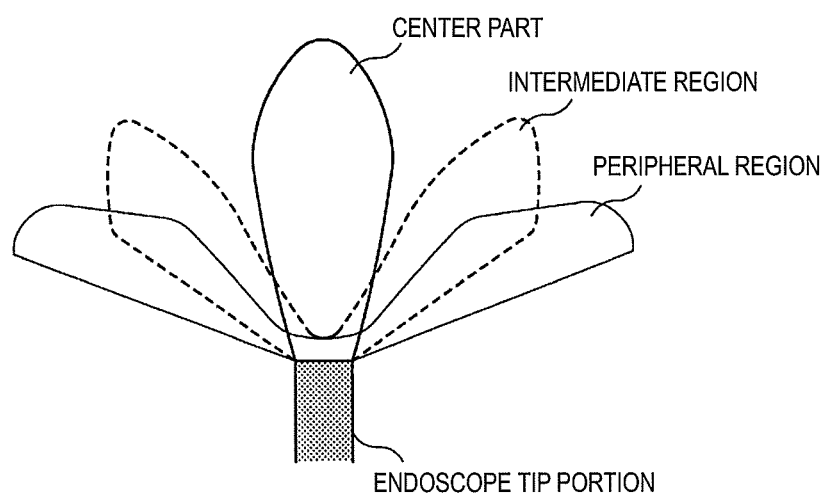
FIG. 18 is an explanatory diagram for describing illumination region control processing in a control unit according to the embodiment.
Figure 19:
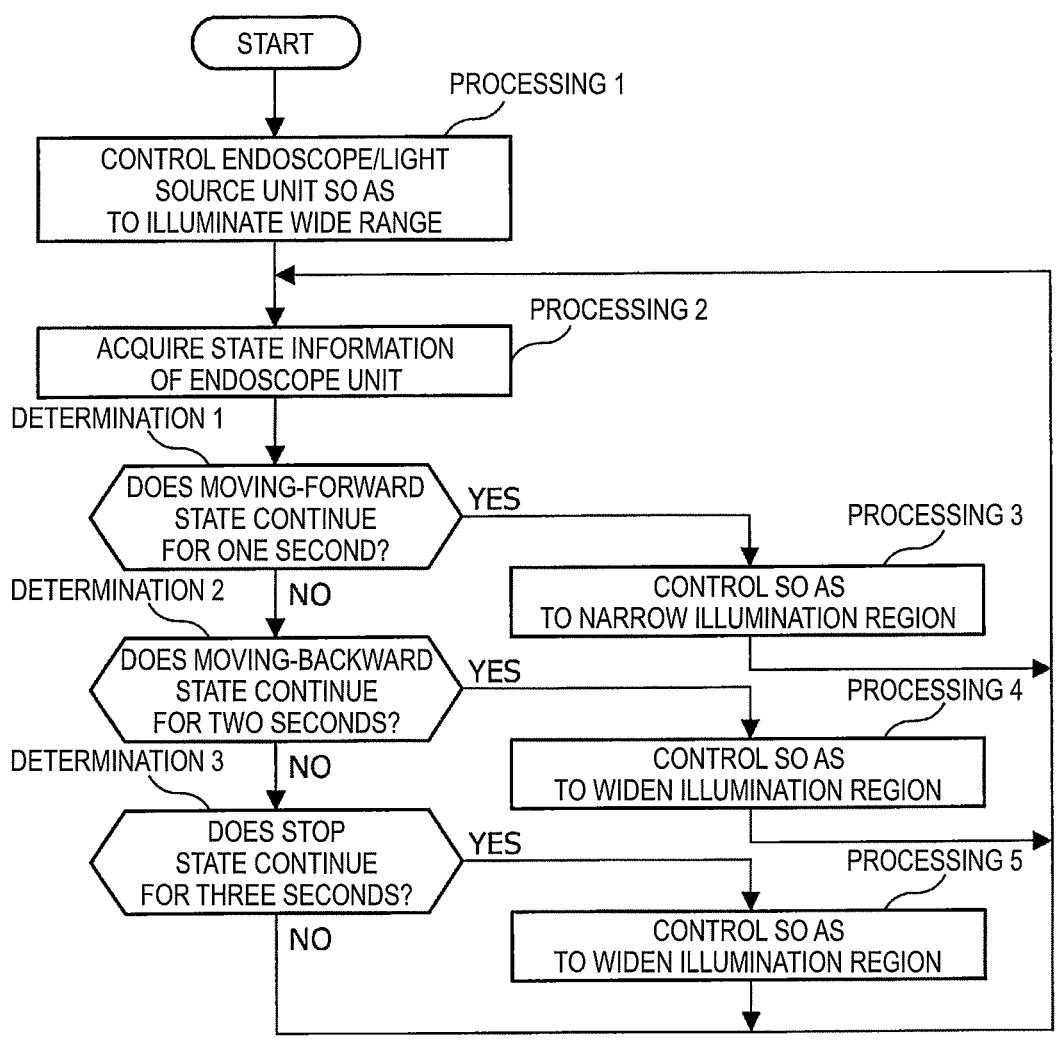
FIG. 19 is a flowchart showing one example of a flow of illumination region control processing in s control unit according to the embodiment.
Figure 20A:
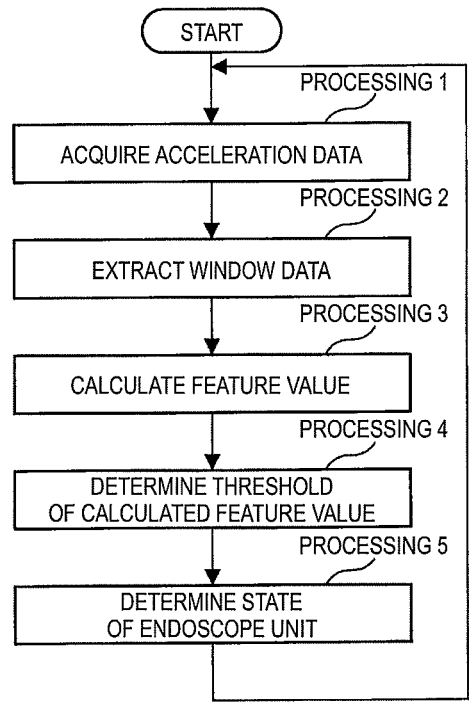
FIG. 20A is a flowchart showing one example of a flow of state determination processing for an endoscope unit in a control unit according to the embodiment.
Figure 20B:
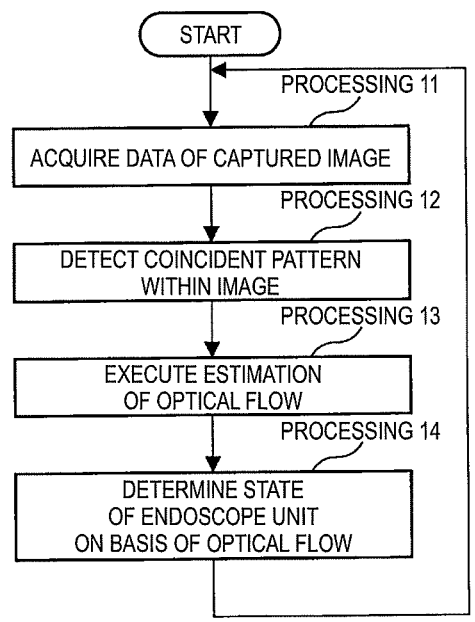
FIG. 20B is a flowchart showing another example of a flow of state determination processing for an endoscope unit in a control unit according to the embodiment.
Figure 21:
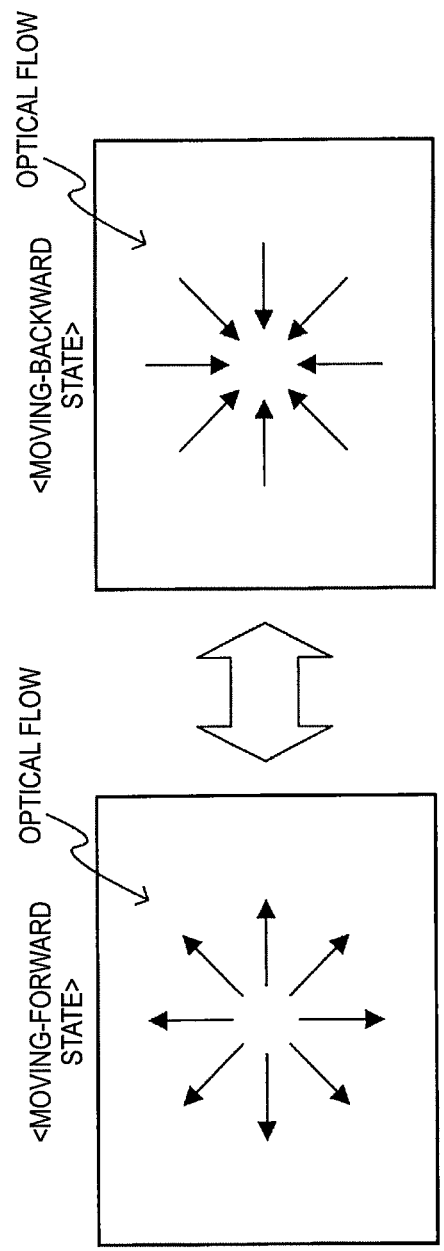
FIG. 21 is an explanatory illustration for describing state determination processing for an endoscope unit in a control unit according to the embodiment.
Figure 22:
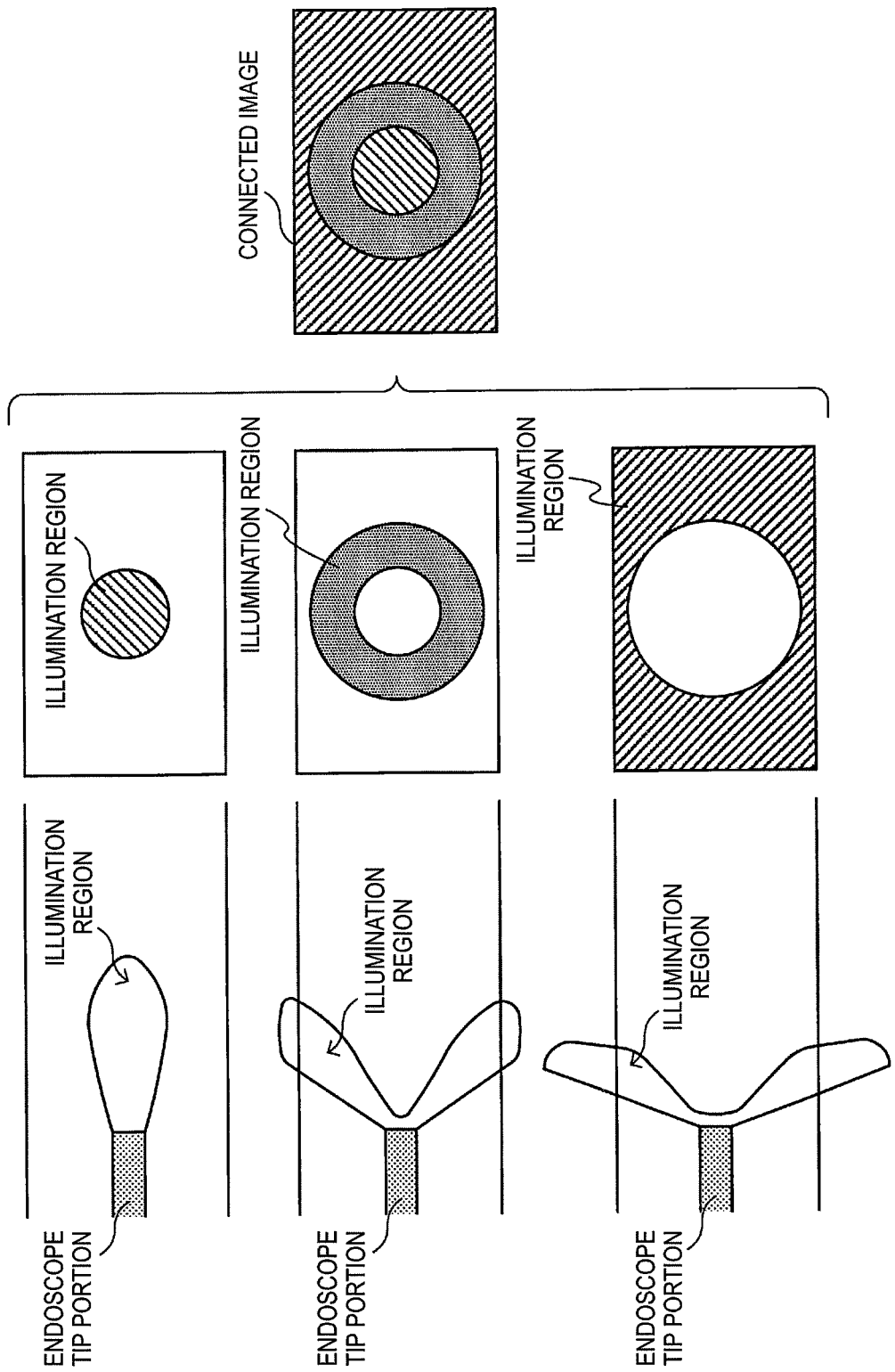
FIG. 22 is an explanatory illustration for describing image connection processing in a control unit according to the embodiment.
Figure 23:
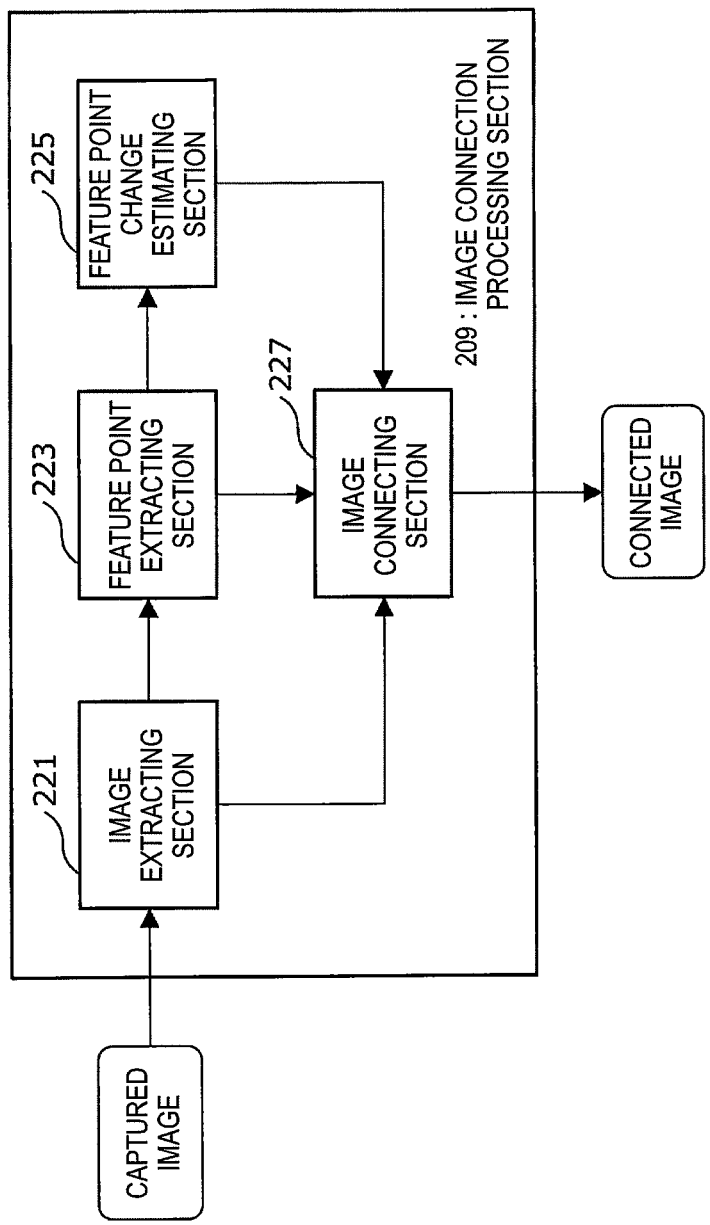
FIG. 23 is a block diagram showing one example of a constitution of an image connection processing section included by a control unit according to the embodiment.

Successively, while referring to FIG. 16 through FIG. 24, description is given in detail for a constitution of the control unit 101 that controls the endoscope apparatus 10 capable of making the radiation angle of illumination lights changeable as described in the above. FIG. 16 is a block diagram showing schematically one example of a constitution of the control unit equipped by the endoscope apparatus according to the present embodiment. FIG. 17 and FIG. 18 each is an explanatory diagram for describing illumination region control processing in the control unit according to the present embodiment. FIG. 19 is a flowchart showing one example of a flow of illumination region control processing in the control unit according to the present embodiment. FIG. 20A is a flowchart showing one example of a flow of state determination processing of the endoscope unit in the control unit according to the present embodiment, and FIG. 20B is a flowchart showing another example of a flow of state determination processing of the endoscope unit in the control unit according to the present embodiment. FIG. 21 is an explanatory illustration for describing the state determination processing of the endoscope unit in the control unit according to the present embodiment, FIG. 22 and FIG. 24 each is an explanatory illustration for describing image connection processing in the control unit according to the present embodiment, and FIG. 23 is a block diagram showing one example of a constitution of an image connection processing section included by the control unit according to the present embodiment.

As having mentioned previously, the control unit 101 according to the present embodiment being one example of the control section is a unit that controls by presiding over the overall function of the endoscope apparatus 10, and controls collectively the working state of each of the endoscope unit 103, the light source unit 105, the imaging unit 107, and the display unit 109, which constitute the endoscope apparatus 10.

As schematically shown in FIG. 16, such a control unit 101 mainly includes a presiding control section 201, and it is preferable that it further includes an operation information acquiring section 203, a data acquiring section 205, an endoscope unit state determining section 207, an image connection processing section 209, an output processing section 211, a display control section 213, and a memory section 215.

The presiding control section 201 is realized by, for example, a CPU, a ROM, a RAM, an input device, a communication device, and the like. The presiding control section 201 is a processing section that integrally controls the operation situations of various kinds of units equipped by the endoscope apparatus 10 according to the present embodiment. Namely, by referring to operation information that has been acquired by the operation information acquiring section 203 at the latter stage and corresponds to various kinds of user's operations by an operator of the endoscope apparatus 10, it is possible for the presiding control section 201 to make the endoscope unit 103, the light source unit 105, the imaging unit 107, and the display unit 109 of the endoscope apparatus 10 execute various kinds of functions desired by an operator.

Moreover, in the endoscope apparatus 10 according to the present embodiment, the endoscope unit 103 or the light source unit 105 operates appropriately, whereby, as having stated previously, it is possible to make the radiation angle of illumination light changeable. With this, it is possible to realize spot-shaped illumination light in which an amount of light in the vicinity of an optical axis in the insertion portion of the endoscope unit 103 is larger than an amount of light around such an optical axis.

The presiding control section 201 controls appropriately the endoscope unit 103 or the light source unit 105, whereby it becomes possible to make an illumination region coaxially changeable by controlling the radiation angle distribution of spot-shaped illumination light at multi stages. For example, as shown in FIG. 17 and FIG. 18, in addition to a general state of controlling illumination light so as to illuminate an observable region of the endoscope unit 103 on the whole, it is possible for the presiding control section 201 to control the radiation angle distribution of illumination light in three stages, such as a state of having made it concentrate in the center part, a state of having made it so as to illuminate a peripheral region of an observable region, and a state of having made it so as to illuminate an intermediate region between the center part and the peripheral region.

By using control of an irradiation region of such illumination light appropriately, the endoscope apparatus 10 according to the present embodiment changes the radiation angle of illumination light correspondingly whether an insertion portion being a part of the endoscope unit 103 having been inserted in the inside of the observation object S is moving in the inside of the observation object S, or has stopped.

That is, when the endoscope unit 103 is being inserted, illumination light is irradiated to only the center part in an observable region of the endoscope unit 103, and then, after a tip portion of the endoscope unit 103 has been positioned at a target part, an illumination region of illumination light is made to be returned to a usual illumination state. With this, when the endoscope unit 103 is being inserted, an amount of light in the peripheral region lowers, and illumination at an inner portion in the lumen at the center part becomes strong. Furthermore, since an amount of light in the peripheral region lowers, it becomes possible to suppress the occurrence rate of a phenomenon that "the brightness of the whole captured image lowers, the overall brightness lowers by AGC, and a dark portion will become further darker".

In this way, when the endoscope unit 103 is being inserted or pulled out, the presiding control section 201 causes the radiation angle distribution of illumination light to be changed intentionally. Accordingly, at the time of inserting the endoscope unit 103, it becomes possible to insert the endoscope unit 103 while confirming the front of the inside of a living body easily. That is, since the forward visibility can be confirmed, the insertion speed of the endoscope unit 103 can be increased more while securing safety, whereby it becomes possible to reduce the burden of a person to be examined.

In concrete terms, it is preferable that when the insertion portion of the endoscope unit 103 is moving forward in the inside of the observation object S, the presiding control section 201 according to the present embodiment makes the radiation angle of illumination light small, and when the insertion portion of the endoscope unit 103 has stopped at the inside of the observation object S or is moving backward in the inside of the observation object S, the presiding control section makes the radiation angle of illumination light large.

One example of a flow of illumination region control processing by the presiding control section 201 as described in the above, is shown in FIG. 19. Under usual conditions, the presiding control section 201 controls the endoscope unit 103 or the light source unit 105 such that a wide range is illuminated (in other words, the whole observable region of the endoscope unit 103 is illuminated) (processing 1).

Subsequently, upon acquiring state information with regard to the state of an endoscope unit from a later-mentioned endoscope unit state determining section 207 (processing 2), the presiding control section 201 executes the following control processing in accordance with the temporal transition of the acquired state information.

That is, the presiding control section 201 determines whether or not the acquisition of the state information indicating that "the insertion portion of the endoscope unit 103 is moving forward" has continued for one second (determination 1). In the case where the moving-forward state is continuing for one second (determination 1—YES), the presiding control section 201 controls the endoscope unit 103 or the light source unit 105 to narrow an illumination region (for example, so as to become a state of illuminating the center part shown in FIG. 17 and FIG. 18) (processing 3).

On the other hand, in the case where the moving-forward state is not continuing for one second (determination 1—NO), the presiding control section 201 determines whether or not the acquisition of the state information indicating that "the insertion portion of the endoscope unit 103 is moving backward" has continued for two seconds (determination 2). In the case where the moving-backward state is continuing for two seconds (determination 2—YES), the presiding control section 201 controls the endoscope unit 103 or the light source unit 105 to widen an illumination region (for example, so as to become a state of illuminating an intermediate region or a periphery region shown in FIG. 17 and FIG. 18, or a state of illuminating the whole observable region) (processing 4).

On the other hand, in the case where the moving-backward state is not continuing for two seconds (determination 2—NO), the presiding control section 201 determines whether or not the acquisition of the state information indicating that "the insertion portion of the endoscope unit 103 has stopped" has continued for three seconds (determination 3). In the case where the stop state is continuing for three seconds (determination 3—YES), the presiding control section 201 controls the endoscope unit 103 or the light source unit 105 to widen an illumination region (for example, so as to become a state of illuminating the whole observable region) (processing 5).

On the other hand, in the case where the stop state is not continuing for three seconds (determination 3—NO), the presiding control section 201 returns to the processing 2 while maintaining the present illumination state, and continues the illumination region control processing.

By performing such processing, in the endoscope apparatus 10 according to the present embodiment, it becomes possible to execute the insertion of the endoscope into the inside of an observation object more promptly, and it becomes possible to reduce the burden of an endoscope operator more. It is thought that such control for an illumination region is useful also in the case where an operator observes the inside of a living body of a person to be examined who exists in a remote place with a remote operation by using the so-called remote medical system, and the like.

In this connection, the number of seconds in each determination shown in FIG. 19 is merely one example, and is not limited to the values shown in FIG. 19. Accordingly, it is possible to set to any value. Moreover, the state information with regard to the state of the endoscope unit output from the endoscope unit state determining section 207 will be described again in the below.

In this connection, in the case where an operator of the endoscope apparatus 10, such as a doctor and a scopist, executes predetermined user's operations, it is possible for the operator to cause an irradiation region of illumination light to be changed with one's own intention without depending on the illumination region control processing by the presiding control section 201 as described in the above.

Moreover, when the insertion portion of the endoscope unit 103 reaches a desired target part and the observation of the target part is started (in other words, when the insertion portion of the endoscope unit 103 has stopped for a predetermined time or more), the presiding control section 201 may cause the radiation angle of illumination light to be changed for the same observation part for example as shown in FIG. 17 and FIG. 18, and may cause a plurality of captured images to be generated for the same observation part by the imaging unit 107. By causing a plurality of captured images to be generated with regard to the same observation part, it becomes possible to generate a connected image as described in the latter stage. The generation processing of such a connected image will be described again in the below.

The operation information acquiring section 203 is realized by, for example, a CPU, a ROM, a RAM, an input device, a communication device, and the like. The operation information acquiring section 203 acquires the operation information corresponding to various kinds of user's operations executed by an operator of the endoscope apparatus 10 for the endoscope apparatus 10. Upon acquiring operation information corresponding to user's operations executed by an operator for various kinds of units constituting the endoscope apparatus 10, the operation information acquiring section 203 outputs the acquired operation information to the presiding control section 201. After having referred to such operation information, the presiding control section 201 performs suitable control for each of the units constituting the endoscope apparatus 10, whereby it becomes possible to realize operations desired by the operator of the endoscope apparatus 10.

For example, upon acquiring the operation information corresponding to the user's operation to the effect that the radiation angle of illumination light is made to be changed, having been executed by an operator of the endoscope apparatus 10, the operation information acquiring section 203 outputs such operation information to the presiding control section 201. Upon acquiring such operation information, without depending on the state of the endoscope unit 103, the presiding control section 201 causes the radiation angle of illumination light to be changed up to the state that an operator wishes. With this, in the endoscope apparatus 10 according to the present embodiment, without depending on the state of the endoscope unit 103, it becomes possible to cause the state of the endoscope apparatus 10 to be changed to the illumination state that an operator desires.

The data acquiring section 205 is realized by, for example, a CPU, a ROM, a RAM, a communication device, and the like. The data acquiring section 205 acquires the image data of a captured image with regard to the inside of an observation object (for example, living body) S generated by the imaging unit 107 of the endoscope apparatus 10. Upon acquiring the above-described image data of the captured image output from the imaging unit 107, the data acquiring section 205 notifies the presiding control section 201 that such image data has been acquired, and, in addition, it is possible to output the acquired image data to the endoscope unit state determining section 207, the image connection processing section 209, the output processing section 211, and the like. Moreover, the data acquiring section 205 may associate the acquired image data of the captured image with time information with regard to the date and time, etc. when having acquired the image data, and then, may record the image data associated with the time information as history information in the memory section 215.

Moreover, in the case where the acceleration sensor 121 is disposed in the endoscope unit 103 of the endoscope apparatus 10 according to the present embodiment, the data acquiring section 205 acquires output information with regard to the acceleration output from the acceleration sensor 121 at any time. Upon acquiring the output information with regard to such acceleration, the data acquiring section 205 outputs the acquired output information with regard to the acceleration to the endoscope unit state determining section 207. Moreover, the data acquiring section 205 may associate the data of the acquired output information with regard to the acceleration with time information with regard to the date and time, etc. when having acquired the data, and then, may record the data associated with the time information as history information in the memory section 215.

The endoscope unit state determining section 207 is realized by, for example, a CPU, a ROM, a RAM, and the like. The endoscope unit state determining section 207 determines the state of the endoscope unit 103 (i.e., whether is moving forward, is moving backward, has stopped, • • • or the like), by using the output value from the acceleration sensor 121 disposed in the endoscope unit 103, or a captured image with regard to the inside of the observation object S output from the imaging unit 107.

In the below, first, while referring to FIG. 20A, description is given concretely for a case where the endo scope unit state determining section 207 uses an output value from the acceleration sensor 121. In the case where the endoscope unit 103 mounts the acceleration sensor 121, it becomes possible for the endoscope unit state determining section 207 to determine the state of the endoscope unit 103 with the following processing by using the output value of the acceleration sensor 121 acquired by the data acquiring section 205.

When the endoscope unit state determining section 207 acquires acceleration data (i.e., data with regard to the output value of the acceleration sensor 121) from the data acquiring section 205 (processing 1), the endoscope unit state determining section 207 extracts window data from the acceleration data on the basis of a range of time window having been set beforehand (processing 2). Subsequently, the endoscope unit state determining section 207 calculates a feature value characterizing such data by using the window data with a predetermined time width (processing 3). It becomes possible for the endoscope unit state determining section 207 to calculate continuously a feature value as described in the above by making such a time window act while making it overlap.

Here, a feature value calculated by the endoscope unit state determining section 207 is not limited specifically, and as a feature value, it is possible to use publicly-known statistics, such as an average value, distributed value, maximum value, square mean value, and the like of the acceleration within a predetermined range of a time window. In generally-used acceleration sensors, even if the sensor is any of an acceleration sensor specialized in one axial direction or an acceleration sensor specialized in three axial directions, since the sensor detects minute vibration etc., a lot of noise is superimposed on the output value of the sensor. However, by calculating a feature value as described in the above by using a time window with a predetermined width, it becomes possible to execute the state determination of the endoscope unit 103 more accurately by reducing the influence of such noise.

Subsequently, the endoscope unit state determining section 207 compares the calculated feature value with a predetermined threshold prescribed beforehand (processing 4). With this, the endoscope unit state determining section 207 can determine a state (i.e., whether is moving forward, is moving backward, has stopped, • • • or the like) of the endoscope unit 103 (processing 5).

Next, while referring to FIG. 20B, description is given concretely for a case where the endoscope unit state determining section 207 performs the state determination of the endoscope unit 103 by using a captured image. In the case of determining a state of the endoscope unit 103 by using a captured image, the endoscope unit state determining section 207 determines a state of the endoscope unit 103 by using a so-called moving body detecting technique. As the moving body detecting technique, there exist, for example, techniques, such as a template matching method and a background estimating method. Especially, in the case where an observation object is an organ in a living body, in many cases, such an organ in a living body does not have a specific pattern. Accordingly, it is difficult to apply techniques using feature point extraction for morphological recognition, such as template matching and background estimation. Then, the endoscope unit state determining section 27 performs state determination for the endoscope unit 103 by using moving body detecting techniques, such as a so-called block matching method or a gradient method.

In concrete terms, upon acquiring the image data of a captured image from the data acquiring section 205 (processing 11), the endoscope unit state determining section 207 detects a coincident pattern within an image by using the moving body detecting techniques as described in the above (processing 12), and executes the estimation of an optical flow on the basis of the obtained coincident pattern (processing 13). Here, even in the case of using any of the above-described techniques, the endoscope unit state determining section 207 will extract a region having a high correlation with a subblock (template) within a noticed image and a subblock within another image the other time. Here, with regard to a captured image under observation with an endoscope, in consideration of a premise that the background also moves at the same speed unlike the usual moving body detection, the size of a template is made large, whereby it becomes possible to cause an amount of calculation to be reduced.

In this connection, basically, in the moving body detection as described in the above, it is important that there exist many parts with differences from peripheries as features within an image. However, in the present embodiment, the speed of a moving body is not estimated, but a movement direction or whether or not it is moving, is estimated. Accordingly, even in the case where the number of feature points is small, it is possible to determine the state of the endoscope unit 103.

Upon estimating an optical flow by doing as described in the above, the endoscope unit state determining section 207 determines a state of the endoscope unit 103 on the basis of the estimated optical flow (processing 14). In concrete terms, as schematically shown in FIG. 21, in the case where the endoscope unit 103 is moving forward, the direction of an optical flow becomes a direction from the center part toward a peripheral part. On the other hand, in the case where the endoscope unit 103 is moving backward, the direction of the optical flow becomes a direction from a peripheral part toward the center part. Moreover, in the case where the endoscope unit 103 has stopped, a large change does not exist in the optical flow. Therefore, the endoscope unit state determining section 207 can determine a state of the endoscope unit 103 by paying its attention to the direction of an optical flow.

In this connection, in the viewpoint of feature points, in a captured image obtained by sprinkling dye for dye endoscopy, it becomes easy to extract feature points. That is, for an observation part, by sprinkling dye that emits fluorescence with a certain specific color tone, concavity and convexity of lesions are emphasized, and specific dyeing for tumors or lesions occurs. With this, it becomes easy to acquire correlation between blocks, and feature point extraction becomes easier. Here, such dye is not limit specifically. However, it is possible to cite, for example, a Lugol's method or toluidine blue dyeing at the time of observing an esophagus, an indigo carmine method or an indigo carmine acetate method at the time of observing a stomach, and a crystal violet method, an indigo carmine method, or a methylene blue method at the time of observing a large intestine. Moreover, also with regard to narrow-band light observation (NBI), since minute blood vessels on a surface can be observes clearly, it is easy to acquire correlation.

In the above, while referring to FIG. 20A through FIG. 21, the state determination processing of the endoscope unit 103 in the endoscope unit state determining section 207 has been described concretely.

The endoscope unit state determining section 207 determines a state of the endoscope unit 103 at any time by doing as described in the above, and outputs the acquired result to the presiding control section 201.

In this connection, in the case where both the output value of the acceleration sensor 121 and a captured image can be used, the endoscope unit state determining section 207 may determine a state of the endoscope unit 103 by the respective methods, and may compare both the obtained results with each other. By comparing the determination result by one method and the determination result by the other method with each other, it becomes possible to determine a state of the endoscope unit 103 more certainly.

The image connection processing section 209 is realized by, for example, a CPU, a ROM, a RAM, and the like. The image connection processing section 209 is a processing section that creates a connected image in which dispersion in luminance value such as being saturated because of too bright due to an amount of light of illumination light or being buried in noise because of too dark has been suppressed, by using a plurality of captured images with respect to the same observation part, by extracting a part of a region in the captured image in accordance with a luminance value for each of the plurality of captured images to obtain an extracted image, and by connecting a plurality of extracted image with each other. Hereinafter, while referring to FIG. 22 through FIG. 24, the image connection processing executed by the image connection processing section 209 according to the present embodiment is described in detail.

Even in the case of having generated a captured image by arranging a tip portion of an endoscope at a desired observation position, in the case of making a luminal organ an observation object, the following phenomena may arise. Namely, there may arise a case where the distribution of the maximum luminance in a captured image is biased toward a peripheral portion so that the luminance of the center part being important as an observation object cannot be obtained, or a case where, conversely, if the luminance of the center part is made higher by narrowing the illuminating to the center part, the luminance of a region close in distance to a camera even at the center part becomes high and an amount of light at a peripheral part becomes insufficient. In the illuminating in general endoscope apparatuses, since the whole irradiation region and the light amount distribution in the region are unchanged, if there is an extremely bright region, the whole amount of light will be lowered by AGC.

In order to solve such phenomena, it may be considered that a photographed image is divided into regions, the brightness of the image is calculated by performing weighting for each of the regions to be observed, and the brightness of the illuminating is changed. With this, it may be considered that even in the case where the luminance of a region unnecessary for observation is high enough to saturate, since the weighting is performed for a region to be observed, it becomes possible to make the influence of the luminance of a region unnecessary for observation small. However, in the method as described in the above, the information with regard to a region having been determined as being unnecessary at the time of observation is saturated, or missing, and cannot be used for anything. However, in the case where it becomes possible to cause the radiation angle distribution of illumination light to be changed as described in the above, it becomes possible to acquire much more information with regard to the inside of an observing object region by the following method.

In concrete terms, in the image connection processing section 209 according to the present embodiment, by using a plurality of captured images with respect to the same observation part, and by connecting respective parts of the plurality of captured image with each other, created is a connected image in which dispersion in luminance value such as being saturated because of too bright due to an amount of light of illumination light or being buried in noise because of too dark has been suppressed.

For example, as schematically shown in FIG. 22, it is assumed that the radiation angle of illumination light is changeable in three stages from a wide radiation angle to a narrow radiation angle, and that three sheets of captured images are created for the same observation part. Here, in each figure shown in FIG. 22, it is assumed that a hatching region is a region where imaging has been performed in a state of suitable illumination light. In this case, the image connection processing section 209 cuts out regions each having a suitable luminance value and connects the regions with each other, whereby one sheet of a connected image can be created. In the connected image to be created, dispersion in luminance value such as being saturated because of too bright due to an amount of light of illumination light or being buried in noise because of too dark is suppressed so that it becomes possible to prevent a loss of image information.

However, in the case where the observation object S is a living body, since a shape in the inside of a living body changes gradually from moment to moment and a camera used for imaging is also in the form of an endoscope, a hand shake tends to occur. Therefore, even if only images with optimal luminance are simply collected from a plurality of captured images and the images are arranges in pixels, it is difficult to perform correct connection.

Then, the image connection processing section 209 according to the present embodiment executes processing described in the below, whereby it becomes possible to execute the creation of a connected image in consideration of a change with time of the observation object S and a hand shake.

The image connection processing section 209 according to the present embodiment includes, as shown in FIG. 23, an image extracting section 221, a feature point extracting section 223, a feature point change estimating section 225, and an image connecting section 227.

The image extracting section 221 is realized by, for example, a CPU, a ROM, a RAM, and the like. The image extracting section 221 compares a plurality of captured images used for creation of a connected image, and extracts a region having a suitable luminance value and contrast from each of the captured images to obtain extracted images. At this time, the image extracting section 221 may execute coordinate transformation, for example, such as transforming an image including distortion due to a super wide angle lens into a plane image for each of the captured images if needed. In this connection, in the case of creating an extracted image from each of the captured images, it is preferable to perform cutting-out for a range wider than a region having a suitable state.

Figure 24:
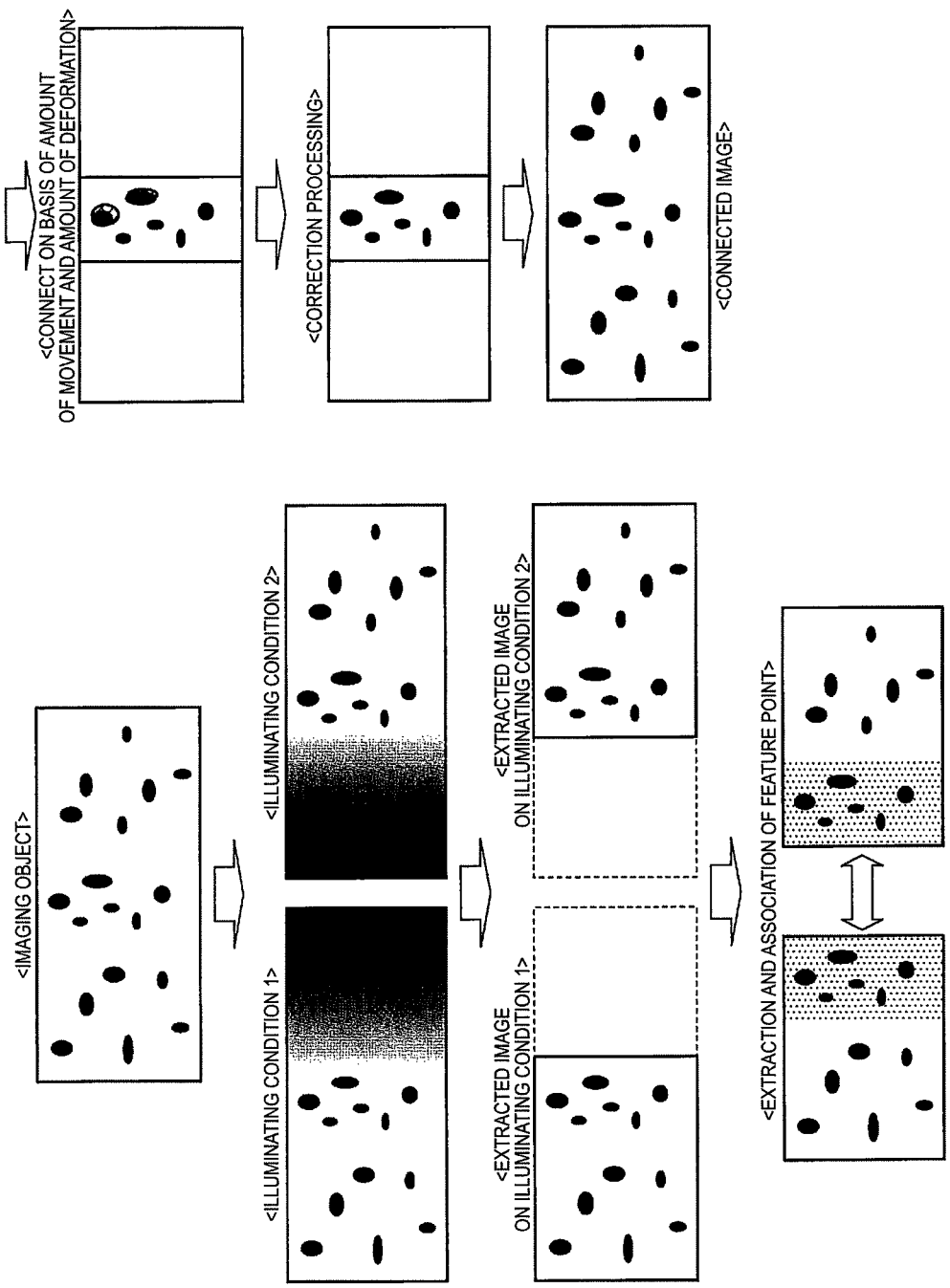
FIG. 24 is an explanatory illustration for describing image connection processing in a control unit according to the embodiment.

For example, it is assumed that at the time of imaging an imaging object as shown on the left side at the uppermost stage in FIG. 24, the imaging has been performed on two kinds of illuminating conditions as shown in FIG. 24. It is assumed that in the captured image on the illuminating condition 1, a loss of a luminance value has occurred at the right side portion of the image, and in the captured image on the illuminating condition 2, a loss of a luminance value has occurred at the left side portion of the image. In this case, the image extracting section 221 creates an extracted image from each of the captured images by performing cutting-out for a range wider than a region having a suitable state.

The extracted images extracted by the image extracting section 221 are output to the feature point extracting section 223 and the image connecting section 227 at the latter stage.

The feature point extracting section 223 is realized by, for example, a CPU, a ROM, a RAM, and the like. The feature point extracting section 223 specifies mutually-overlapping portions (overlapping portion) for the respective created extracted-images, and in addition, extracts feature points from the specified overlapping portions, and executes association of the respective feature points.

For example, in an example shown in FIG. 24, the feature point extracting section 223 compares two extracted images, and specifies overlapping portions by a publicly-known method. In an example shown on the left side at the lowermost stage in FIG. 24, the feature point extracting section 223 specifies portions shown with hatching as overlapping portions, and executes extraction and association of feature points with regard to such overlapping portions.

Upon executing the specification of overlapping portions and the extraction and association of feature points by doing in the above way, the feature point extracting section 223 outputs the obtained results to the feature point change estimating section 225 and the image connecting section 227 each mentioned later.

The feature point change estimating section 225 is realized by, for example, a CPU, a ROM, a RAM, and the like. The feature point change estimating section 225 estimates a size of movement and deformation of the extracted feature points over time between the respective extracted images. That is, the feature point change estimating section 225 estimates each of an amount of movement and an amount of deformation on the supposition that the movement and deformation of the feature points have occurred at the capturing interval when the captured images becoming the basis of the respective extracted images have been captured. The estimating method of such an amount of movement and an amount of deformation is not limited specifically, and it is possible to estimate by a publicly-known method on the basis of the general knowledge etc. with regard to a capturing timing (imaging timing) in the imaging unit 107, the pulsation of the observation object S, and the like.

Upon performing estimation with regard to a temporal change of the feature points by doing in the above way, the feature point change estimating section 225 outputs the obtained estimation results to the image connecting section 227 mentioned later.

The image connecting section 227 is realized by, for example, a CPU, a ROM, a RAM, and the like. The image connecting section 227 executes connection processing for the extracted images created by the image extracting section 221 on the basis of the information with regard to the feature points obtained by the feature point extracting section 223 and the information with regard to the temporal change of the feature points obtained by the feature point change estimating section 225.

In concrete terms, the image connecting section 227 connects the extracted images while correcting an amount of movement and an amount of deformation on the supposition that the feature points have moved and deformed when the captured images becoming the basis of the respective extracted images have been captured. With this, as shown on the right side at the uppermost stage in FIG. 24, one image will be created from the plurality of extracted images.

Moreover, in the created connected image, as shown on the right side at the uppermost stage in FIG. 24, a case where the feature points do not coincide with each other perfectly due to a hand shake, also may occur. At this time, it is possible for the image connecting section 227 to remove a hand shake part existing in the connected image by performing correction processing using publicly-known hand shake correction techniques. Moreover, it is also possible for the image connecting section 227 to execute correction processing for a luminance value and contrast and the other image correction processing, such as removal of ghost in the connected part. With this, as shown on the right side at the lowermost stage in FIG. 24, a connected image from which a change with time of the observation object S, a hand shake, etc. have been removed will be created.

Upon creating a connected image at any time by doing in the above way, the image connecting section 227 outputs the obtained connected image to the output processing section 211.

In the above, while referring to FIG. 22 through FIG. 24, the image connection processing executed by the image connection processing section 209 according to the present embodiment has been described in detail.

The output processing section 211 is realized by, for example, a CPU, a ROM, a RAM, an output device, a communication device, and the like. The output processing section 211 outputs the image data of the captured images acquired by the data acquiring section 205 and the image data of the connected images created by the image connection processing section 209 for an operator of the endoscope apparatus 10. The output processing section 211 makes the display unit 109 display various kinds of acquired image data while cooperating with the display control section 213, whereby it becomes possible to provide an operator of the endoscope apparatus 10 with an observed image obtained by observing the inside of the observation object (for example, living body) S.

In this connection, it is possible for the output processing section 211 to output the image data of the captured image acquired by the data acquiring section 205 and the image data of the connected image created by the image connection processing section 209 as a printed matter, or to output them to an external information processing apparatus, a server, etc. as data. In the case where the output processing section 211 outputs these image data to the external information processing apparatus, the server, etc., it becomes possible to associate automatically various kinds of image data captured by the endoscope apparatus 10 with an electronic medical record etc. stored in the above-described information processing apparatus, the server, etc., or to paste an image on an electronic medical record etc. automatically.

Moreover, the output processing section 211 receives the state determination result of the endoscope unit state determining section 207 under the control of the presiding control section 201, and may notify an operator of the endoscope apparatus 10 of a guide and a state determination result stating that "the endoscope unit 103 is moving forward and backward, is vibrating, or is rotating". By outputting such a notice for an operator, for example, it becomes possible to draw attention to an operator so as not to cause blurring etc. when the operator of the endoscope apparatus 10 is going to capture a still image of an observation part. Such a notice is useful, especially, when a plurality of captured images is generated for the same observation part for the purpose of creating a connected image as described in the above.

Moreover, in the case where the observation object S is a living body, since the heat resistance of the inside of the living body is low, if the same position is illuminated with high luminance continuously for a certain time, there is a possibility that the observation part causes heat damage. Then, in response to the state determination result of the endoscope unit state determining section 207, under the control of the presiding control section 201, the output processing section 211 may notify the warning indicating that "there is possibility of heat damage" to an operator.

In this connection, such notice and warning may be output as character data through the display control section 213, may be output as voice data, such as sound and an alarm, or may be output as vibration of the grade which does not surprise an operator.

The display control section 213 is realized by, for example, a CPU, a ROM, a RAM, an output device, a communication device, and the like. The display control section 213 performs display control at the time of displaying various kinds of results output from the output processing section 211 on an output device, such as a display equipped by the display unit 109 of the endoscope apparatus 10, an output device disposed at the outside of the endoscope apparatus 10, or the like. With this, it becomes possible for an operator of the endoscope apparatus 10 to grasp various kinds of results on the spot.

The memory section 215 is one example of a memory device equipped by the control unit 101 of the endoscope apparatus 10, and is realized by a RAM, a storage device, or the like equipped by the control unit 101. In the memory section 215, recorded are various kinds of data bases used by the control unit 101 according to the present embodiment at the time of executing various kinds of processing. Moreover, in the memory section 215, various kinds of history information may be recorded. Furthermore, in the memory section 215, appropriately recorded are various parameters or interim progress of processing for which necessity to save has been caused when the control unit 101 according to the present embodiment has performed some processing, or various kinds of data bases, programs, or the like. For this memory section 215, it is possible for the presiding control section 201, the operation information acquiring section 203, the data acquiring section 205, the endoscope unit state determining section 207, the image connection processing section 209, the output processing section 211, the display control section 213, and the like to execute read/write processing freely.

In the above, one example of the function of the control unit 101 according to the present embodiment has been shown. The respective constitution components described in the above may be constituted by using general-purpose components and circuits, or may be constituted by hardware specialized for the functions of the respective constitution components. Moreover, a CPU or the like may perform all the functions of the respective constitution components. Therefore, in accordance with the technical level when the present embodiment is executed from time to time, it is possible to appropriately change the constitution to be used.

In this connection, it is possible to produce computer programs for realizing each function of the control unit according to the present embodiment as described in the above, and to mount them in a personal computer and the like. Moreover, it is possible to provide also a computer-readable recording medium in which such computer programs are stored. The recording media may be, for example, a magnetic disc, an optical disc, a magneto-optical disc, a flash memory, or the like. Moreover, the above-described computer programs may be distributed, for example, through networks, without using a recording medium.

As described in the above, in the endoscope apparatus 10 according to the present embodiment, it becomes possible to execute the insertion of the endoscope unit 103 promptly, and it becomes possible to reduce each of the burden of an operator of the endoscope apparatus 10 and the burden of a person to be examined. Moreover, in the endoscope apparatus 10 according to the present embodiment, in the case of acquiring a captured image with regard to an observation object, it is possible to suppress a loss of information as much as possible by preventing luminance saturation, whereby the information from an obtained image can be utilized to the utmost.

<With Regard to Hardware Configuration of Control Unit>

Figure 25:
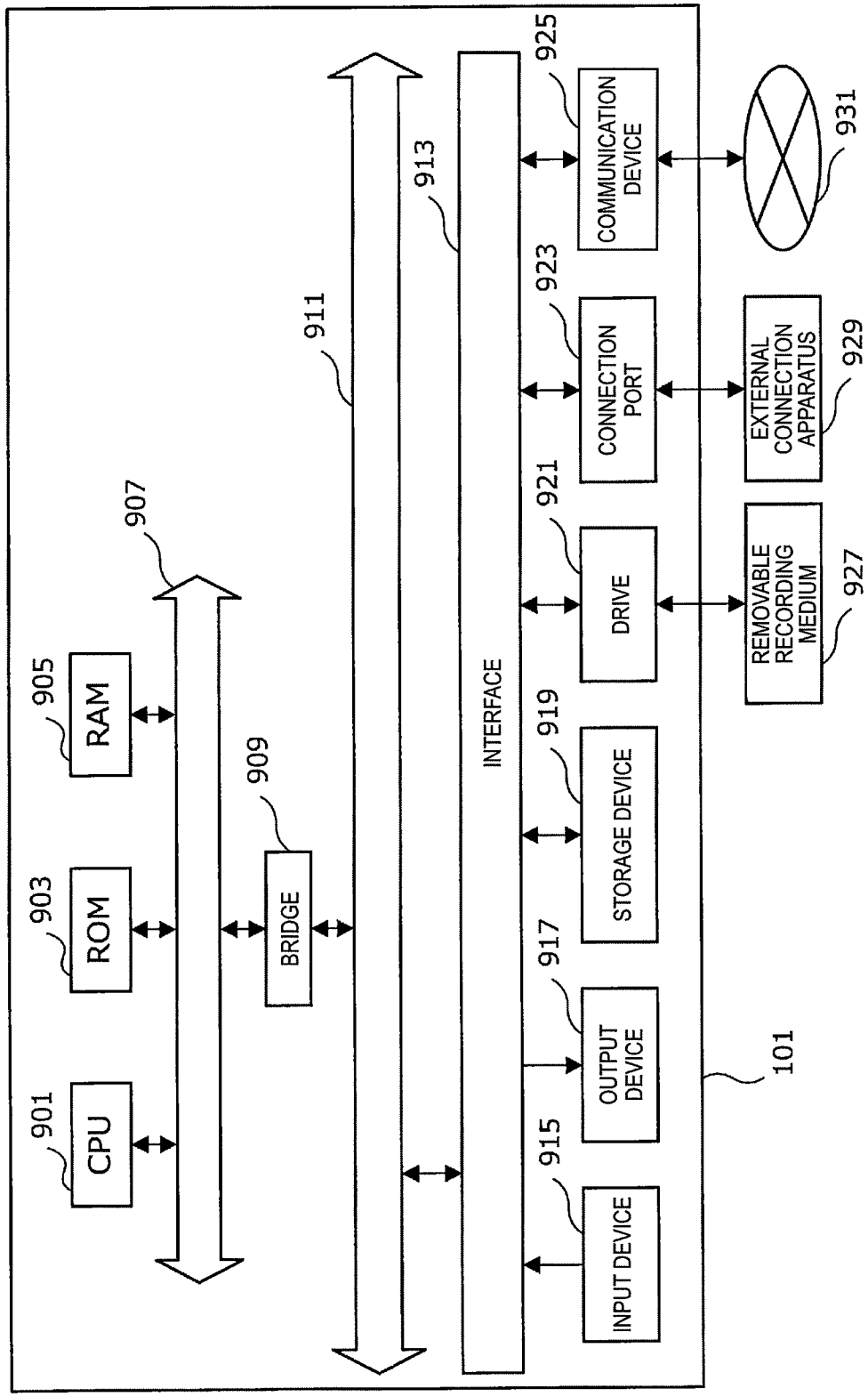
FIG. 25 is a block diagram showing one example of a hardware configuration of a control unit according to the embodiment.

Next, the hardware configuration of the control unit 101 of the endoscope apparatus 10 according to the embodiment will be described in detail with reference to FIG. 25. FIG. 25 is a block diagram for describing the hardware configuration of the control unit 101 according to the embodiment of the present disclosure.

The control unit 101 mainly includes a CPU 901, a ROM 903, and a RAM 905. Furthermore, the control unit 101 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing apparatus and a control apparatus, and controls the overall operation or a part of the operation of the control unit 101 according to various programs recorded in the ROM 903, the RAM 905, the storage device 919, or a removable recording medium 927. The ROM 903 stores programs, operation parameters, and the like used by the CPU 901. The RAM 905 primarily stores programs used the CPU 901 and parameters and the like varying as appropriate during the execution of the programs. These are connected with each other via the host bus 907 including an internal bus such as a CPU bus.

The host bus 907 is connected to the external bus 911 such as a PCI (Peripheral Component Interconnect/Interface) bus via the bridge 909.

The input device 915 is an operation means operated by a user, such as a mouse, a keyboard, a touch panel, buttons, a switch and a lever, for example. Also, the input device 915 may be a remote control means (a so-called remote controller) using, for example, infrared light or other radio waves, or may be an external connection apparatus 929 such as a mobile phone or a PDA conforming to the operation of the control unit 101. Furthermore, the input device 915 generates an input signal on the basis of, for example, information which is input by a user with the above operation means, and includes an input control circuit or the like for outputting the input signal to the CPU 901. The user can input various data to the control unit 101 and can instruct the control unit 101 to perform various types of processing by operating this input device 915.

The output device 917 includes a device capable of visually or audibly notifying a user of acquired information. Such a device includes a display device such as a CRT display device, a liquid crystal display device, a plasma display device, an EL display device and a lamp, an audio output device such as a speaker and a headphone, a printer, a mobile phone, a facsimile machine, and the like. For example, the output device 917 outputs a result obtained by various types of processing performed by the control unit 101. Specifically, the display device displays, in the form of text or images, a result obtained by various types of processing performed by the control unit 101. On the other hand, the audio output device converts an audio signal including reproduced audio data, sound data, and the like into an analog signal, and outputs the analog signal.

The storage device 919 is a device for storing data configured as an example of a storage unit of the control unit 101. The storage device 919 includes, for example, a magnetic storage device such as a HDD (Hard Disk Drive), a semiconductor storage device, an optical storage device, a magneto-optical storage device, or the like. This storage device 919 stores programs to be executed by the CPU 901 and various types of data, externally obtained various types of data, and the like.

The drive 921 is a reader/writer for a recording medium, and is built in the control unit 101 or attached externally thereto. The drive 921 reads information recorded in the attached removable recording medium 927 such as a magnetic disk, an optical disc, a magneto-optical disk, or a semiconductor memory, and outputs the read information to the RAM 905. Furthermore, the drive 921 can write records in the attached removable recording medium 927 such as a magnetic disk, an optical disc, a magneto-optical disk, or a semiconductor memory. The removable recording medium 927 is, for example, a DVD medium, an HD-DVD medium, a Blu-ray (registered trademark) medium, or the like. In addition, the removable recording medium 927 may be a CompactFlash (CF; registered trademark), a flash memory, an SD memory card (Secure Digital Memory Card), or the like. Further, the removable recording medium 927 may be, for example, an IC card (Integrated Circuit Card) equipped with a non-contact IC chip, an electronic appliance, or the like.

The connection port 923 is a port for allowing devices to directly connect to the control unit 101. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, a High-Definition Multimedia Interface (HDMI, registered trademark) port, and the like. By connecting the external connection apparatus 929 to this connection port 923, the control unit 101 directly acquires various types of data from the external connection apparatus 929 and provides various types of data to the external connection apparatus 929.

The communication device 925 is a communication interface including, for example, a communication device or the like for connecting to a communication network 931. The communication device 925 is, for example, a communication card or the like for a wired or wireless LAN (Local Area Network), Bluetooth (registered trademark), or WUSB (Wireless USB). Further, the communication device 925 may be a router for optical communication, a router for ADSL (Asymmetric Digital Subscriber Line), a modem for various types of communication, or the like. This communication device 925 can transmit and receive signals and the like in accordance with a predetermined protocol, for example, such as TCP/IP on the Internet and with other communication devices, for example. In addition, the communication network 931 connected to the communication device 925 includes a network and the like which is connected in a wire or wireless manner, and may be, for example, the Internet, a home LAN, infrared communication, radio wave communication, satellite communication, or the like.

The above illustrates an example of the hardware configuration capable of realizing the functions of the control unit 101 according to the embodiment of the present disclosure. Each of the above structural elements may be realized using a general-purpose member, or may also be realized using hardware specialized in the function of each structural element. Consequently, it is possible to appropriately modify the hardware configuration to be used according to the technical level at the time of carrying out the present embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An endoscope apparatus, including:

an endoscope unit at least a part of which is inserted into an inside of an observation object and that propagates an image of the inside of the observation object irradiated with illumination light;

a light source unit that emits the illumination light illuminating the inside of the observation object to the endoscope unit;

an imaging unit that captures an image of the inside of the observation object having been propagated from the endoscope unit and generates a captured image of the inside of the observation object; and a control section that performs driving control for the endoscope unit, the light source unit, and the imaging unit, in which a radiation angle of the illumination light is changeable, and the control section changes the radiation angle of the illumination light in accordance with whether an insertion portion being a part of the endoscope unit having been inserted into the inside of the observation object is moving in the inside of the observation object or has stopped.

(2)

The endoscope apparatus according to (1), in which the illumination light is spot-shaped illumination light in which an amount of light in vicinity of an optical axis in the insertion portion is larger than an amount of light in periphery of the optical axis, and the control section makes the radiation angle of the illumination light small when the insertion portion is moving forward in the inside of the observation object, and the control section makes the radiation angle of the illumination light large when the insertion portion has stopped in the inside of the observation object, or is moving backward in the inside of the observation object.

(3)

The endoscope apparatus according to (1) or (2), in which in the endoscope unit, an acceleration sensor is disposed, and the control section determines, on the basis of output information from the acceleration sensor, whether the insertion portion is moving or has stopped.

(4)

The endoscope apparatus according to any one of (1) to (3), in which the control section calculates an optical flow of the captured image output from the imaging unit, and determines, on the basis of the calculated optical flow, whether the insertion portion is moving or has stopped.

(5)

The endoscope apparatus according to any one of (1) to (4), in which the control section, when the insertion portion has stopped in the inside of the observation object, causes the radiation angle of the illumination light to be changed for a same observation part, and causes a plurality of the captured images to be generated with respect to the same observation part by the imaging unit, extracts a part of a region within a captured image in accordance with a luminance value for each of the plurality of captured images to obtain an extracted image, and connects a plurality of the extracted images with each other, thereby creating a connected image in which dispersion in luminance value caused by an amount of light of the illumination light has been suppressed.

(6)

The endoscope apparatus according to (5), in which the control section extracts a feature point for each of the extracted images and associates the extracted feature points among a plurality of the extracted images, thereby specifying overlappingly-imaged regions, estimates temporal changes of the feature points caused by different imaging timings among the plurality of extracted images, and connects the plurality of extracted images with each other in consideration of the temporal changes of the feature points.

(7)

The endoscope apparatus according to (5) or (6), in which when the plurality of captured images are generated for the same observation part, in a case of having detected movement of the insertion portion, the control section outputs a guide indicating that the insertion portion has moved, for an operator.

(8)

The endoscope apparatus according to any one of (1) to (7), in which the control section causes the radiation angle of the illumination light to be changed on the basis of an operation signal corresponding to an operation executed by an operator.

(9)

The endoscope apparatus according to any one of (1) to (8), in which in an inside of the endoscope unit, an illuminating optical system that propagates the illumination light to an observation part, is disposed, and in the inside of the endoscope unit, at least a part of the illuminating optical system moves, whereby the radiation angle of the illumination light changes.

(10)

The endoscope apparatus according to any one of (1) to (8), in which the light source unit includes a light source section that emits the illumination light and a coupling section capable of being connected with a light guide disposed in the endoscope unit, and an incident angle of the illumination light entering the light guide in the coupling section changes, whereby the radiation angle of the illumination light changes.

(11)

The endoscope apparatus according to (10), in which in the coupling section, a coupling optical system that causes the illumination light whose incident angle to the light guide has been controlled, to be coupled to the light guide, is disposed.

(12)

The endoscope apparatus according to (10), in which in the coupling section, a reflective optical system that causes the illumination light emitted from the light source section to be reflected, or a refractive optical system that causes the illumination light to be refracted, and a coupling optical system that causes the illumination light to be coupled to the light guide, are disposed, and the reflective optical system or the refractive optical system is made to be moved, whereby on an incident surface to the coupling optical system, a separation distance between an optical axis of the coupling optical system and an incident position of the illumination light is made to be changed, and the incident angle of the illumination light is made to be changed.

(13)

The endoscope apparatus according to (10), in which an angle formed by an optical axis of the coupling section and an optical axis of the light guide is made to be changed, whereby the incident angle of the illumination light is made to be changed.

(14)

The endoscope apparatus according to (10), in which a beam size of the illumination light on an incident surface of the illumination light to the light guide is made to be changed, whereby the incident angle of the illumination light is made to be changed.

(15)

The endoscope apparatus according to (10), in which a divergence angle of the illumination light having been emitted from the light source section is made to be changed, whereby the incident angle of the illumination light is made to be changed.

(16)

A control method of an endoscope apparatus that includes an endoscope unit at least a part of which is inserted into an inside of an observation object and that propagates an image of the inside of the observation object irradiated with illumination light, a light source unit that emits the illumination light illuminating the inside of the observation object to the endoscope unit, and an imaging unit that captures an image of the inside of the observation object having been propagated from the endoscope unit and generates a captured image of the inside of the observation object, in which a radiation angle of the illumination light is changeable, the control method including:

by a control section that performs driving control for the endoscope unit, the light source unit, and the imaging unit, determining whether an insertion portion being a part of the endoscope unit having been inserted into the inside of the observation object is moving in the inside of the observation object or has stopped; and changing the radiation angle of the illumination light in accordance with a state of the insertion portion.

REFERENCE SIGNS LIST

10 endoscope apparatus
101 control unit
103 endoscope unit
105 light source unit
107 imaging unit
109 display unit
111,117 light guide
113 illuminating optical system
115 objective optical system
119 image forming optical system
121 acceleration sensor
131 light source section
133 coupling section
135 multi-mode optical fiber
137 driving mechanism
139 control section
141 memory section
151 collimator lens
153 incident angle adjusting mechanism
155 coupling optical system
201 presiding control section
203 operation information acquiring section
205 data acquiring section
207 endoscope unit state determining section
209 image connection processing section
211 output processing section
213 display control section
215 memory section
221 image extracting section
223 feature point extracting section
225 feature point change estimating section
227 image connecting section

The invention claimed is:

1. An endoscope apparatus, comprising:
an endoscope including a tip configured to be inserted into an inside of an observation object and propagate an image of the inside of the observation object irradiated with illumination light;
a light source configured to emit the illumination light illuminating the inside of the observation object to the endoscope, the light source being optically coupled to the endoscope and outputting light from the tip;
an imager configured to capture the image of the inside of the observation object having been propagated from the endoscope and generate a captured image of the inside of the observation object; the image being optically coupled to the endoscope; and
control circuitry configured to control a radiation angle of illumination light output by the tip in accordance whether the tip inside of the observation object is moving or has stopped,
wherein the illumination light output by the light source has a distribution in which a light intensity output by the light source in a vicinity of a central optical axis of the tip is larger than a light intensity output by the light source in a periphery of the optical axis of the tip, and
the control circuitry is configured to decrease the radiation angle of the illumination light output by the tip when the tip is moving forward inside of the observation object and to increase the radiation angle of the illumination light output by the tip when the tip is stopped inside of the observation object or is moving backward inside of the observation object.

2. The endoscope apparatus according to claim 1,
further comprising an acceleration sensor in the endoscope, and
the control circuitry is configured to receive an output from the acceleration sensor and determine, on a basis of the output of the acceleration sensor, whether the tip is moving or has stopped.

3. The endoscope apparatus according to claim 1, wherein the control circuitry is configured to calculate an optical flow of a captured image output from the imager, and determine, on a basis of the calculated optical flow, whether the tip is moving or has stopped.

4. The endoscope apparatus according to claim 1, wherein the control circuitry is configured to,
on condition that the tip has stopped in the inside of the observation object, change the radiation angle of the illumination light for a same observation part, and cause a plurality of captured images to be generated with respect to the same observation part by the imager,
extract a part of a region within a captured image in accordance with a luminance value for each of the plurality of captured images to obtain an extracted image, and
connect a plurality of the extracted images with each other, thereby creating a connected image in which dispersion in luminance value caused by an intensity of the illumination light has been suppressed.

5. The endoscope apparatus according to claim 4, wherein the control circuitry is configured to:
extract a feature point for each extracted image and associate the extracted feature points among a plurality of extracted images, thereby specifying overlappingly-imaged regions,
temporal changes of the feature points caused by different imaging timings among the plurality of extracted images, and
connect the plurality of extracted images with each other in consideration of the temporal changes of the feature points.

6. The endoscope apparatus according to claim 4, wherein when the plurality of captured images are generated for the same observation part, in a case of having detected movement of the tip, the control circuitry is configured to output a guide indicating that the tip has moved, for an operator.

7. The endoscope apparatus according to claim 1, wherein the control circuitry is configured to change the radiation angle of the illumination light on a basis of an operation signal corresponding to an operation executed by an operator.

8. The endoscope apparatus according to claim 1, further comprising
an optical coupler between the light source and a light guide in the endoscope, and
the optical coupler changes an incident angle of the illumination light output by the light source, whereby the radiation angle of the illumination light incident on the light guide changes.

9. The endoscope apparatus according to claim 8, wherein optical coupler includes coupling optics that control the incident angle of the illumination light output to the light guide.

10. The endoscope apparatus according to claim 8,
wherein optical coupler includes reflective optics that reflect the illumination light emitted from the light source, or a refractive optics that refracts the illumination light, and coupling optics that direct the illumination light to the light guide, and
the reflective optics or the refractive optics is movable in response to the control circuitry to change the illumination light incident on the light guide by changing a separation distance between an optical axis of the coupling optics and an incident position of the illumination light on the light guide.

11. The endoscope apparatus according to claim 8, wherein an angle formed by an optical axis of the optical coupler and an optical axis of the light guide is changed response to the control circuitry, whereby the incident angle of the illumination light on the light guide is changed.

12. The endoscope apparatus according to claim 8, wherein, in response to the control circuitry, the optical coupler changes a beam size of the illumination light on an incident surface of the light guide.

13. The endoscope apparatus according to claim 8, wherein, in response to the control circuitry, the optical coupler changes a divergence angle of the illumination light emitted from the light source, to be incident on the light guide.

14. The endoscope apparatus according to claim 1, wherein the control circuitry is external to the endoscope.

15. A control method of an endoscope apparatus that includes an endoscope including a tip inserted into an inside of an observation object and that propagates an image of the inside of the observation object irradiated with illumination light, a light source that emits the illumination light illuminating the inside of the observation object to the endoscope, and an imager that captures an image of the inside of the observation object having been propagated from the endoscope and generates a captured image of the inside of the observation object, the control method comprising:
determining whether the tip having been inserted into the inside of the observation object is moving in the inside of the observation object or has stopped, wherein the illumination light output by the light source has a distribution in which a light intensity output by the light source in a vicinity of a central optical axis in the tip is larger than a light intensity output by the light source in a periphery of the optical axis in the tip; and decreasing a radiation angle of the illumination light output by the tip when the tip is moving forward inside of the observation object and increasing the radiation angle of the illumination light output by the tip when the tip is stopped inside of the observation object or is moving backward inside of the observation object.

16. The endoscope apparatus according to claim 8, wherein the optical coupler is external to the endoscope.

* * * * *